United States Patent
Hettrick et al.

(10) Patent No.: US 10,646,713 B2
(45) Date of Patent: May 12, 2020

(54) SYSTEMS, DEVICES, AND ASSOCIATED METHODS FOR TREATING PATIENTS VIA RENAL NEUROMODULATION TO REDUCE A RISK OF DEVELOPING COGNITIVE IMPAIRMENT

(71) Applicant: Medtronic Ardian Luxembourg S.a.r.l., Luxembourg (LU)

(72) Inventors: Douglas Hettrick, Andover, MN (US); Gabriel Lazarus, Bethesda, MD (US)

(73) Assignee: MEDTRONIC ARDIAN LUXEMBOURG S.A.R.L., Luxembourg (LU)

(*) Notice: Subject to any disclaimer, the term of this patent is extended or adjusted under 35 U.S.C. 154(b) by 179 days.

(21) Appl. No.: 15/481,508

(22) Filed: Apr. 7, 2017

(65) Prior Publication Data
US 2018/0236235 A1 Aug. 23, 2018

Related U.S. Application Data

(60) Provisional application No. 62/461,950, filed on Feb. 22, 2017.

(51) Int. Cl.
*A61N 1/36* (2006.01)
*A61N 1/05* (2006.01)
(Continued)

(52) U.S. Cl.
CPC ....... *A61N 1/36082* (2013.01); *A61N 1/3606* (2013.01); *A61N 1/36017* (2013.01);
(Continued)

(58) Field of Classification Search
CPC .. A61N 1/0551; A61N 1/3605; A61N 1/3606; A61N 1/36082; A61N 1/36189;
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| WO | WO-1994007446 A1 | 4/1994 |
| WO | WO-1995025472 A1 | 9/1995 |

(Continued)

OTHER PUBLICATIONS

Hasegawa, et al., "Renal Denervation in the Acute Phase of Ischemic Stroke Provides Brain Protection in Hypertensive Rats", Stroke, 2017, pp. 14.

(Continued)

*Primary Examiner* — Deborah L Malamud
(74) *Attorney, Agent, or Firm* — Snell & Wilmer L.L.P.

(57) ABSTRACT

Methods for reducing a risk associated with developing cognitive impairment, including dementia, with therapeutic renal neuromodulation and associated systems and methods are disclosed herein. Sympathetic nerve activity can contribute to several cellular and physiological conditions associated with an increased risk of developing dementia in later life. One aspect of the present technology is directed to methods for improving a patient's calculated risk score for developing dementia. Other aspects of the present technology are directed to reducing a likelihood of developing dementia in patients presenting one or more dementia risk factors in middle age. Renal sympathetic nerve activity can be attenuated to improve a patient's risk of developing dementia. The attenuation can be achieved, for example, using an intravascularly positioned catheter carrying a therapeutic assembly, e.g., a therapeutic assembly configured to use electrically-induced, thermally-induced, and/or chemically-induced approaches to modulate the renal sympathetic nerve.

10 Claims, 10 Drawing Sheets

(51) Int. Cl.
  *A61B 18/00* (2006.01)
  *A61B 18/14* (2006.01)
(52) U.S. Cl.
  CPC . *A61B 18/1492* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61N 1/0551* (2013.01); *A61N 1/36117* (2013.01)
(58) Field of Classification Search
  CPC ........ A61N 1/36; A61N 1/36135; A61N 1/00; A61N 1/05; A61N 1/36128; A61N 1/3727; A61B 2018/00434; A61B 5/4035; A61B 5/0031
  See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster, Jr. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0002349 A1 | 1/2002 | Flaherty et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0045909 A1 | 3/2003 | Gross et al. |
| 2003/0050635 A1 | 3/2003 | Truckai et al. |
| 2003/0050681 A1 | 3/2003 | Pianca et al. |
| 2003/0060848 A1 | 3/2003 | Kieval et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0181963 A1 | 9/2003 | Pellegrino et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0015193 A1 | 1/2004 | Lamson et al. |
| 2004/0082978 A1 | 4/2004 | Harrison et al. |
| 2004/0215186 A1 | 10/2004 | Cornelius et al. |
| 2005/0004522 A1 | 1/2005 | Katoh et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2012/0130289 A1 | 5/2012 | Demarais et al. |
| 2012/0130345 A1 | 5/2012 | Levin et al. |

(56) References Cited

U.S. PATENT DOCUMENTS

| | | | |
|---|---|---|---|
| 2012/0172837 A1 | 7/2012 | Demarais et al. | |
| 2013/0237780 A1* | 9/2013 | Beasley | A61B 18/18 600/309 |
| 2015/0196762 A1* | 7/2015 | Amurthur | A61N 1/36117 604/21 |

FOREIGN PATENT DOCUMENTS

| | | |
|---|---|---|
| WO | WO-1995031142 A1 | 11/1995 |
| WO | WO-1997036548 A1 | 10/1997 |
| WO | WO-1998042403 A1 | 10/1998 |
| WO | WO-1999000060 A1 | 1/1999 |
| WO | WO-2001022897 A1 | 4/2001 |
| WO | WO-2001070114 A1 | 9/2001 |
| WO | WO-2003022167 | 3/2003 |
| WO | WO-2003/082080 | 10/2003 |
| WO | WO-2005030072 A1 | 4/2005 |
| WO | WO-2005041748 A2 | 5/2005 |
| WO | WO-2005/110528 A1 | 11/2005 |
| WO | WO-2006041881 A2 | 4/2006 |
| WO | WO-2006105121 A2 | 10/2006 |
| WO | WO-2007008954 A2 | 1/2007 |
| WO | WO-2007078997 A2 | 7/2007 |
| WO | WO-2008049084 A2 | 4/2008 |

OTHER PUBLICATIONS

Lambert, et al., "Cognitive Performance in Patients with Resistant Hypertension Following Renal Sympathetic Denervation", EuroIntervention, 2013, vol. 9 (6), pp. 665-667.
Search Report dated Oct. 17, 2013 for European Application No. 13159256.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter", Journal of the American College of Cardiology, 1999; 33; pp. 972-984.
Beale et al., "Minimally Invasive Treatment for Varicose Ceins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries influence of Age, Sex, Anatomic Variation, and Left Ventricular Hypertrophy or Dilation", Circulation, 1992, vol. 86(1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, Granted Oct. 28, 2015, Date of Opposition Jul. 27, 2016, 34 pp.

(56) References Cited

OTHER PUBLICATIONS

Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
OZ, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol, 93, Jun. 1, 2004, 4 pages.
Purerfellner, Helmut et al., Pulmonary Vein Stenosis Following Catheter Ablation of Atrial Fibrillation, Curr. Opin. Cardio. 20:484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneder, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http//:www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Curtis, J.J., et al., "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Doumas, Michael et al., "Renal Nerve Ablation for Resistant Hypertension: The Dust Has Not Yet Settled." The Journal of Clinical Hypertension. 2014; vol. 16, No. 6, 2 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700, dated Feb. 5, 2013, 61 pages.

(56) References Cited

OTHER PUBLICATIONS

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W.H., et al. "Combined embolization and percutaneous radiofrequency ablation of a solid renal tumor." *Am. J. Roentgenol*, 174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response," *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetises rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothennal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation," European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Messerli, Franz H. et al. "Renal Denervation for Resistant Hypertension: Dead or Alive?" Healio: Cardiology today's Intervention, May/Jun. 2014, 2 pages.

Millard, F. C., et al, "Renal Embolization for ablation of function in renal failure and hypertension." Postgraduate Medical Journal, 65 729-734, (1989).
Miler, Reed, "Finding a Future for Renal Denervation With Better Controlled Trials." Pharma & Medtech Business Intelligence, Article # 01141006003, Oct. 6, 2014, 4 pages.
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Pedersen, Amanda, "TCT 2012: Renal denervation deuce makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicetomy" Am J Surgery (1948) pp. 48-68.
Renal Denervation (RDN), Sympiicity RDN System Common Q&A (2011), 4 pages, http://www.medtronic.com/rdn/mediakit/RDN%20FAQ.pdf.
Schauerte, P., et al. "Catheter Ablation of Cardiac Autonomic Nerves for Prevention of Vagal Atrial Fibrillation." Circulation, 102:2774-2780 (2000).
Schlaich, Markus et al,, "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversable renal denervation on haemodynamic and excretory functions on the ipsilateral and contralateral kidney in the cat." Hypertension, 4: 181-188 (1986).
Stouffer, G. A. et al., "Catheter-based renal denervation in the treatment of resistant hypertension." Journal of Molecular and Cellular Cardiology, vol. 62, 2014, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).

(56) References Cited

OTHER PUBLICATIONS

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock., M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Oishi, Emi, MD, et al., "Day-to-Day Blood Pressure Variability and Risk of Dementia in a General Japanese Elderly Population—The Hisayama Study," Circulation 2017; 136:516-525; DOI: 10.1161/CIRCULATIONAHA. 116.025667, Aug. 8, 2017.
Azizi, Michael, et al., "Optimum and Stepped Care Standardised Antihypertensive Treatment With or Without Renal Denervation for Resistant Hypertension (DENERHTN): a multicentre, open-label, randomised controlled trial" www.thelancet.com, http://dx.doi.org/10.1016/S0140-6736(14)61942-5; Published Jan. 26, 2015.
Bakris, George L., MD et al., "Impact of Renal Denervation on 24-Hour Ambulatory Blood Pressure" Journal of the American College of Cardiology, vol. 64, No. 11, Sep. 16, 2014.
Baroni, Matteo, et al., "Effects of Renal Sympathetic Denervation on Arterial Stiffness and Blood Pressure Control in Resistant Hypertensive Patients: A Single Centre Prospective Study" High Blood Press Cardiovasc Prev, Oct. 12, 2015.
Brant, Mathias C., MD et al. "Effects of Renal Sympathetic Denervation on Arterial Stiffness and Central Hemodynamics in Patients With Resistant Hypertension" Journal of the American College of Cardiology, vol. 60, No. 19, Nov. 6, 2012.
Bronzuoli, Maria Rosanna et al., "Targeting Neuroinflammation in Alzheimer's Disease" Journal of Inflammation Research, pp. 199-120, Nov. 3, 2016.
Dorr, Oliver et al., "Beneficial Effects of Renal Sympathetic Denervation on Cardiovascular Inflammation and Remodeling in Essential Hypertension" Clin Res Cardiol 104:175-184, 2015.
Frost, Shaun et al., "Oclular Biomarkers for Early Detection of Alzheimer's Disease" Journal of Alzheimer's Disease, 22 pp. 1-16, Jun. 8, 2010.
Hasegawa, Yu, MD et al., "Renal Denervation in the Acute Phase of Ischemic Stroke Provides Brain Protection in Hypertensive Rats" Journal of the American Heart Association, http://stroke.ahajournals.org/content/early/2017/02/28/STROKEAHA.116.015782, pp. 1-14, Feb. 28, 2017.
Iadecola, Costantino, MD et al., "Impact of Hypertension on Cognitive Function" http://hyper.ahajournals.org, pp. e67-e94, Dec. 2016.
Johnson, Keith A. et al., "Brain Imaging in Alzheimer Disease" Cold Spring Harb Perspect Med 2012; 2: A006213; www.perspectivesinmedicine.org.
Kairo, Kazuomi et al., "Effect of Catheter-Based Renal Denervation on Morning and Nocturnal Blood Pressure" Hypertension htttyp://hyper.ahajounals.org, pp. 1-13, Dec. 2015.
Kilander, Lena et al., "Hypertension Is Related to Cognitive Impairment" Department of Geriatrics and Departmenr of Clinical Neurosciences, pp. 780-786, Oct. 6, 1997.
Kivipelto, Miia et al., "Risk Score for the Prediction of Dementia Rise in 20 Years Among Middle Aged People: a Longitudinal, Population-Based Study", Lancet Neurol, http://neurology.thelancet.com, vol. 5 pp. 735-741, Sep. 2006.
Koyama, Alain et al., "The Role of Peripheral Inflammatory Markers in Dementia and Alzheimer's Disease: A Meta-Analysis" J Gerontol A Biol Sci Med Sci. Apr. 2013 68(4): 433-440.
Lambert, Gavin M et al., "Cognitive Performance in Patients With Resistant Hypertension Following Renal Sympathetic Denervation" EuroIntervention: 2013; 9:665-667.
McDonald, Claire et al., "Blood Pressure Variability and Cognitive Decline in Older People: a 5-year Longitudinal Study" Journal of Hypertension, vol. 34, No. 1, 2016, pp. 1-8.
Metti, Andrew L., et al., "How Predictive of Dementia are Peripheral Inflammatory Markers in the Elderly?" Neurodengener Dis Manag. Dec. 1, 2012, 2(6): 609-622.
Mortenson, Kai et al., "Catheter-Based Renal Sympathetic Denervation Improves Central Hemodynamics and Arterial Stiffness: A Pilot Study" The Journal of Clinical Hypertension, vol. 14, No. 12, Dec. 2012, pp. 861-870.
Nakagawa, Takashi et al., "Renal Denervation Prevents Stroke and Brain Injury via Attenuation of Oxidative Stress in Hypertensive Rats" J Am Heart Assoc., 2013;2:e000375.
Okon, Thomas et al., "Invasive Aortic Pulse Wave Velocity as a Marker for Arterial Stiffness Predicts Outcome of Renal Sympathetic Denervation" EuroIntervention, Aug. 2016;12, pp. 684-692.
Schiller, Alicia M. et al., "Renal Nerves Dynamically Regulate Renal Blood Flow in Conscious, Healthy Rabbits" Am J Physiol Regul Integr Comp Physiol, 310:R156-R166, 2016.
Schlaich, Markus P., "Effects of Renal Denervation on Sympathetic Activation, Blood Pressure, and Glucose Metabolism in Patients With Resistant Hypertension" Frontiers in Physiology, Feb. 2, 2012, vol. 3, Article 10, pp. 1-7.
Seals, Douglas R. et al., "Chronic Sympathetic Activation" Perspectives in Diabetes, vol. 53, Feb. 2004.
Semke, Galina et al., "The Long-Term Cerebroprotective Efficiency of Renal Denervation in Resistant Hypertensive Patients" Abstracts, Wolters Fluwer Health, Inc., e497, 2016.
Singh-Manoux, Archana et al., "Interleukin-6 and C-Reactive Protein as Predictors of Cognitive Decline in Late Midlife" American Academy of Neurology, vol. 83, Aug. 5, 2014 pp. 486-493.
Zuern, Christine S., et al., "Effects of Renal Sympathetic Denervation on 24-Hour Blood Pressure Variability" Frontiers in Physiology, vol. 3, Article 134, May 10, 2012, pp. 1-8.
Abell, et al., "Association between systolic blood pressure and dementia in the Whitehall II cohort study: role of age, duration, and threshold used to define hypertension", The European Heart Journal, 2018, pp. 1-7.
Abell, et al., "Risk of dementia is increased in 50-year-olds with blood pressure below the current threshold for hypertension", The European Heart Journal, accessed Jun. 13, 2018, 4 pages, https://www.escardio.org/The-ESC/Press-Office/Press-releases/risk-of-dementia-is-increased-in-50-year-olds-with-blood-pressure-below-the-curr.
Cohut, Maria, "Even slightly elevated blood pressure increases dementia risk", Medical News Today, accessed Jun. 13, 2018, 5 pages, https://www.medicalnewstoday.com/articles/322116.php.

\* cited by examiner

*Arterial Vasculature*

*Venous Vasculature*

Renal Denervation Preclinical Efficacy:
Review of 66 Treated and 64 Naïve Swine

| Group N=Arteries or kidneys | % Non-functional Area | Cortical Axon Area per mm² | Mean NE (pg/mg) |
|---|---|---|---|
| Naïve 7 day N=64 | 14.6 ± 8.0 | 207.2 ± 134.6 | 264.8 ± 82.9 |
| Symplicity 7 day N=54 | 56.9 ± 28.3 | 66.8 ± 84.6 (68% Decrease) | 92.7 ± 92.7 (65% Decrease) |
| Spyral 7 Day N=12 | 47.3 ± 26.5 | 97.4 ± 73.1 (54% Decrease) | 88 ± 75 (68% Decrease) |

SYSTEMS, DEVICES, AND ASSOCIATED METHODS FOR TREATING PATIENTS VIA RENAL NEUROMODULATION TO REDUCE A RISK OF DEVELOPING COGNITIVE IMPAIRMENT

CROSS-REFERENCE TO RELATED APPLICATION(S)

This application claims the benefit of U.S. Provisional Application No. 62/461,950, filed on Feb. 22, 2017, which is incorporated herein by reference in its entirety.

TECHNICAL FIELD

The present technology relates generally to apparatuses, systems, and methods for reducing a risk associated with developing cognitive impairment, such as dementia, and/or for improving one or more measurable physiological indicators corresponding to the progression of dementia using renal neuromodulation.

BACKGROUND

Dementia generally relates to the neurological symptoms that occur when the brain is affected by diseases and conditions that affect cognitive abilities, such as memory recall and formation, problem-solving capabilities and planning, brain processing speed and others. The World Health Organization estimates that nearly 50 million people worldwide are currently affected by cognitive impairment associated with dementia, and the rate of incidence of dementia among older adults is drastically increasing. While many forms of dementia have been identified, certain population groups can be affected by more than one form concurrently. Alzheimer's disease, the most common form of dementia, is a condition in which the chemistry and structure of the brain change, eventually leading to brain cell death during disease progression. Vascular cognitive impairment indicates a range of cognitive deficits from mild impairment to more severe cases, termed vascular dementia, and is generally described as a significant decline in thinking skills that is caused by conditions that block or reduce blood flow to the brain or parts of the brain, ultimately resulting in cell deprivation of life-essential oxygen and nutrients.

Vascular cognitive impairment, Alzheimer's disease, and other forms of dementia are chronic and progressive, and typically present as irreversible deterioration in cognitive function beyond what is expected of normal aging. Dementia, in all its forms, currently lacks serious disease-modifying treatments and with an aging population, 7.7 million new cases are expected every year. As dementia has physical, psychological, social and economic impact on patients as well as caregivers, families and society, there is a need for treatments that effectively reduce the incidence of dementia, such as the incidence of vascular cognitive impairment, vascular dementia, and/or Alzheimer's disease, or provide other improvements in prognosis and outcomes for patients at risk of developing dementia.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 8A is a display table illustrating results from a study to determine the effects of renal denervation on cortical axon density and mean norepinephrine concentration in animal subjects.

FIG. 9 illustrates a dementia risk calculator for determining a patient's dementia risk score in accordance with an embodiment of the present technology.

DETAILED DESCRIPTION

Figure 1:
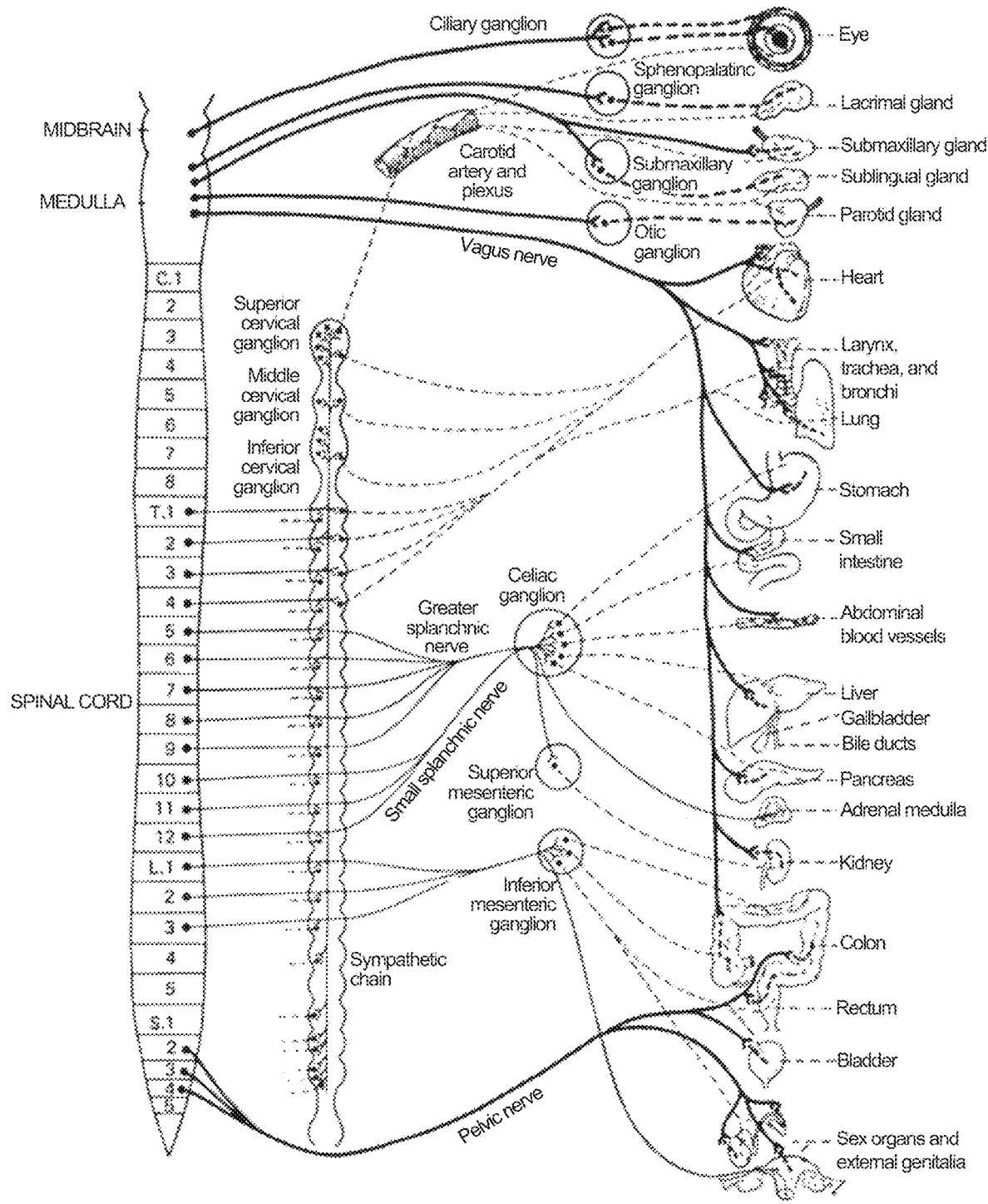
FIG. 1 is a conceptual illustration of the sympathetic nervous system (SNS) and how the brain communicates with the body via the SNS.

The present technology is directed to apparatuses, systems, and methods for treating patients via renal neuromodulation to reduce a risk of such patients developing a form of dementia and/or to improve one or more measurable physiological indicators corresponding to the progression of dementia of the patients. For example, some embodiments of the present technology include performing therapeutically-effective renal neuromodulation on a patient to reduce the risk of occurrence of vascular cognitive impairment (e.g., vascular dementia) and/or other forms of dementia (e.g., Alzheimer's disease). In a particular embodiment, for example, the patient has a measurable risk of developing dementia. In some embodiments, the patient is middle-aged (e.g., 45-65 years old). Other embodiments of the present technology include performing therapeutically-effective renal neuromodulation on a patient to reduce severity of neurological symptoms relating to dementia. Further embodiments include performing therapeutically-effective renal neuromodulation on a patient to slow a rate of progression of neurological symptoms relating to dementia.

As discussed in further detail below, and in various embodiments, forms of dementia can include vascular cognitive impairment (e.g., vascular dementia), Alzheimer's disease, dementia with Lewy bodies, fronto-temporal dementia, or other rarer forms of dementia. As discussed in greater detail below, renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-9. The embodiments can include, for example, modulating nerves proximate (e.g., at or near) a renal artery, a renal vein, and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-9.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. DEMENTIA

Dementia is an inclusive diagnosis for diseases and conditions that display progressive neurological cognitive decline in patients. Neurological symptoms associated with dementia can include, for example, memory loss and difficulties with thinking, problem-solving or language as well as changes in behavior and mood. The etiology of dementia, in all its forms, is uncertain; however evidence suggests that incidence of brain damage by diseases, such as Alzheimer's disease, a series of strokes, cranial blood vessel blockage or narrowing, a genetic condition, infection, and others, cause irreversible and progressive damage to parts of the brain. While changes to the brain tissue (e.g., cellular damage and/or death, loss of brain cell connections, and/or presence of Lewy bodies, plaques or tangles, etc.) may initially be small, neurological symptoms become severe enough to affect daily life as disease conditions progress.

A. Types of Dementia and Progression

As used herein, "dementia" refers to any form of chronic or persistent cognitive disorder (e.g., affecting mental processes) caused by a brain disease or injury and that is indicated by memory disorders or decline, personality changes and impaired reasoning that is severe enough to reduce a patient's ability to perform everyday activities. Despite the many forms of dementia recognized, Alzheimer's disease and vascular dementia accounts for the majority of dementia cases (e.g., about 80%). Alzheimer's disease, as well as other less common forms of dementia (e.g., dementia with Lewy-bodies, Creutzfeldt-Jakob disease) are caused by deleterious depositions of proteins or protein fragments as well as nerve cell damage and death in the brain. "Vascular dementia" includes a variety of forms of dementia that exhibit deleterious alterations to the brain's blood vessels. Such alterations to cerebral blood vessels can ultimately block or reduce blood flow to the brain or regions of the brain that subsequently results in brain cell death and/or atrophy.

Alzheimer's disease is typically characterized by the accumulation of abnormal β-amyloid protein plaques deposited around brain cells and internal structure changes (e.g., neurofibrillary tau protein tangles) to neurons in the brain that cause destruction of chemical connections between brain cells (Iadecola, C. et al., *Hypertension,* 2016, 68: e67-e94). Soluble oligomers of β-amyloid are elevated in the Alzheimer's diseased brain due to increased production of the β-amyloid peptide and its impaired removal. Alzheimer's disease is, however, a multifactorial disorder and is also characterized by oxidative stress, mitochondrial damage, glutamate excitotoxicity, and neuroinflammation, in addition to the neurofibrillary tangle formation and β-amyloid plaques, which collectively lead to synaptic and neuronal dysfunction and death (Bronzuoli, M. R., et al., *J Inflamm Res,* 2016, 9: 199-208).

Vascular dementia is derived primarily from vascular disease which reduces cerebral perfusion, further causing oxidative stress and neurodegeneration. Vascular disease may also result in brain white matter atrophy and abnormalities, infarct, inflammation and reduced glucose metabolism. Blood vessel damage caused by, for example, arterial hypertension, vessel remodeling and stiffness, or vasculitis, along with other vascular damage caused by metabolic and/or hemodynamic disorders (e.g., diabetes, congestive heart failure, obesity), directly affect brain pathology. "Vascular cognitive impairment" refers to the spectrum of cognitive deficits that are caused by vascular factors, including stroke. As such, vascular cognitive impairment includes those deficits beyond normal cognitive decline associated with aging.

While normal aging is associated with expected cognitive decline, "mild cognitive impairment" is classified as an intermediate stage between the expected cognitive decline associated with normal aging and the more serious decline associated with dementia. Patients affected with mild cognitive impairment can have problems with memory, executive function (e.g., thinking and decision-making ability), and language that is beyond what is expected with normal age-related changes. While mild cognitive impairment increases a risk associated with the development of dementia, some patients' neurological condition does not progress to more severe stages.

B. Risk Factors Associated with Development of Dementia

Dementia is a disease category encompassing complex and multifactorial disorders that are known to be caused by many contributing factors. However, many earlier-identifiable conditions and maladies in a patient are recognized as being either contributory factors and/or predictors of a likelihood that a patient will experience cognitive decline and/or develop dementia. In particular, many underlying conditions, diseases and other abnormalities detectable in middle-aged patients (e.g., about 45-65 years old, about 50-70 years old, about 50-65 years old, etc.), may affect the likelihood of the patient developing dementia at older age (e.g., within about 5 years, within about 10 years, within about 20 years, etc.). Such underlying conditions and diseases constitute dementia predictors or risk factors. For example, chronic hypertension, systolic blood pressure variability, systemic inflammation, atherosclerosis, cardiovascular diseases, incidence of stroke and obesity have been shown to be correlative with the incidence of dementia (Iadecola, C., et al., *Hypertension,* 2016, 68: e67-e94; Kilander, L., et al., *Hypertension,* 1998, 31: 780-786; McDonald, C. et al., *J Hypertens.,* 2016, epub 34:000-000; Koyama, A. et al., *J Gerontol A Biol Sci Med Sci.,* 2013, 68(4): 433-440; Metti, A. L. and Cauley, J. A., *Neurodegener Dis Manag.*, 2012, 2(6): 609-622; Singh-Manoux, A., et al., *Neurology,* 2014, 83: 486-493).

Although there is a spectrum of cognitive decline in patients from normative values associated with aging and those values attributable to disease, it has been documented that primary aging and respective changes to the vasculature is associated with progressive, chronic activation of the peripheral sympathetic nervous system (SNS) (Seals, D. R., and Bell, C., *Diabetes,* 2004, 53: 276-284). As shown in FIG. 1, the SNS is a branch of the autonomic nervous system along with the enteric nervous system and parasympathetic nervous system. The SNS is primarily an involuntary bodily control system typically associated with stress responses. It is always active at a basal level (called sympathetic tone) and becomes more active during times of stress. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. The SNS regulates the function of virtually all human organ systems by localized release of catecholamines (e.g., norepinephrine) from sympathetic nerve terminals innervating these tissue and organ systems, spillover of norepinephrine from vascular neuro-muscular junctions (the primary source of norepinephrine in plasma), and by systemic circulation of catecholamines (e.g., epinephrine, norepinephrine) released from the adrenal gland in response to acute, transient stress or threats. Long-term variations in basal levels, increases in basal levels due to aging, as well as spikes of circulating catecholamines from hyperactivity of the SNS responding to life circumstances can also exert more enduring regulatory effects on gene expression by altering constitutive gene expression profiles in a wide variety of tissues and organ systems.

Correlative links between activation of the SNS and high blood pressure, systemic inflammation, arterial stiffness, atherosclerosis, metabolic disorders, insulin resistance, end organ damage, risk of stroke (e.g., acute ischemic stroke, lacunar stroke, transient ischemic attack (TIA), hemorrhagic stroke, etc.) and other cardiovascular conditions have been established. Many of these conditions and diseases have been shown to be associated with age-related cognitive decline and/or have been established as risk factors for the development of dementia in aging patients. For example, chronic arterial hypertension has been established as a risk factor for both Alzheimer's disease and vascular dementia, and midlife hypertension may negatively influence the probability of late-life cognitive decline (Iadecola, C., et al., *Hypertension,* 2016, 68: e67-e94).

Without being bound by theory, hypertension disrupts the structure and function of blood vessels, including cerebral blood vessels, which can lead to ischemic damage in white matter regions of the brain as well as possibly promote plaque formation and neurofibrillary tangles consistent with Alzheimer's disease pathology (Iadecola, C., et al., *Hypertension,* 2016, 68: e67-e94). For example, hypertension is associated with changes in the structure of vascular walls caused by remodeling and stiffening of the vasculature. Hypertension-induced hypertrophy of smooth muscle cells can result in increased thickness of the vessel walls and concomitant narrowing of the vessel lumen. Likewise, deposition of collagen and fibronectin can inwardly remodel the vessel walls causing narrowing, and further elastin fragmentation of the vessel wall can increase stiffness of the vessels. In cerebral arteries, remodeling and increased stiffness of the blood vessels diminishes blood flow to white matter regions that are responsible for cognitive function. Additionally, inflammatory reactions associated with vascular remodeling can cause reactive oxygen species and protease upregulation causing potential disruption of the blood-brain barrier (Id.).

Biomolecules, such as catecholamines and other neuropeptides, are known to be involved in the modulation of blood pressure. As an example, radiotracer dilution has demonstrated increased renal norepinephrine spillover rates in patients with essential hypertension. At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands. As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine spillover rates in patients with essential hypertension, particularly so in young and middle-aged hypertensive subjects, which in concert with increased norepinephrine spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced SNS overactivity.

An additional risk factor associated with and predictive of impaired cognitive decline and dementia in patients includes increased blood pressure variability (e.g., 24 hour blood pressure variability, daytime blood pressure variability) (McDonald, C. et al., *J Hypertens.,* 2016, epub 34:000-000). In particular, daytime blood pressure variability was associated with poorer cognitive function at baseline and was also found predictive of greater decline over a five-year follow-up. While greater blood pressure variability was associated with poorer cognitive outcome among hypertensives, blood pressure variability was predictive of cognitive decline irrespective of chronic high blood pressure (Id.). Without being bound by theory, increased blood pressure variability may be associated with small vessel cerebrovascular disease and has demonstrated an association with greater numbers of white matter lesions as seen by brain imaging (e.g., magnetic resonance imaging (MRI), computed topography (CT)) (Id.).

Hypertension is also an important risk factor for cerebrovascular pathology leading to stroke (Iadecola, C., et al., *Hypertension,* 2016, 68: e67-e94). For example, vascular alterations induced by hypertension can contribute to cognitive impairment or risk of future cognitive impairment by leading to hypoperfusion, ischemic and hemorrhagic stroke, as well as white matter injury (Id.). As hypertension is associated with an increased risk of stroke, and stroke, in turn, increases the risk of dementia, patients at risk of stroke or having had a history of one or more strokes, have increased risk (e.g., predictive) of future cognitive decline (Id.).

Chronic activation of the SNS is also associated with elevated levels of inflammatory cytokines, such as interleukin-6 (IL-6) and other inflammatory markers, such as C-reactive protein (CRP). Increased levels of inflammatory biomarkers, IL-6 and CRP, have been shown to be predictors of cognitive decline in late midlife as well as contributors to the underlying pathology and mechanisms of dementia, including the neurofibrillary tangles and amyloid plaques found in Alzheimer's disease (Singh-Manoux, A., et al., *Neurology*, 2014, 83: 486-493; Metti, A. L. and Cauley, J. A., *Neurodegener Dis Manag.*, 2012, 2(6): 609-622). Moreover, IL-6 affects lipid metabolism and triglyceride production as well as stimulates the hypothalamic-pituitary-adrenal axis, which is associated with hypertension, obesity and insulin resistance, and which further contributes to conditions leading to vascular cognitive impairment (Id.). Additionally, hypertension is associated with chronic vascular inflammation, secretion of IL-6 from endothelial cells and smooth muscle cells, and corresponding induction of CRP (Dörr, O., et al., *Clin Res Cardiol*, 2015, 104: 175-184). Progressive vascular changes due to hypertension and vascular inflammation further contribute to atherosclerosis and reduced blood flow. Atherosclerosis in extracranial as well as intracranial arteries supplying the brain accelerates development of atherosclerotic lesions that impair blood flow and are major sites of thrombogenesis (Iadecola, C., et al., *Hypertension*, 2016, 68: e67-e94). In certain studies, an increased level of CRP was associated with a 45% increased risk of dementia and a higher level of IL-6 was associated with a 32% increased risk of dementia (Koyama, A. et al., *J Gerontol A Biol Sci Med Sci.*, 2013, 68(4): 433-440).

Age-associated stimulation of the SNS increases with adiposity and middle- and older-aged adults with progressive accumulation of body fat and/or who have lower activity (higher sedentary) levels are more likely to generate higher levels of plasma norepinephrine concentrations and spillover rates that further exacerbate vascular changes and contribute to deleterious blood pressure increases (Seals, D. R., and Bell, C., *Diabetes*, 2004, 53: 276-284).

In addition to increasing age, chronic high blood pressure, increased blood pressure variability, increased inflammation, atherosclerosis and/or vessel stiffening/hardening, and obesity, additional risk factors that can be considered in establishing a predictive risk assessment for the development of dementia in a patient can include, for example, level of education (e.g., low education), gender (male), hypercholesterolemia, smoking, and low activity/exercise level (Kivipelto, M., et al. *Lancet Neurol*, 2006, 5: 735-741).

In addition to predisposition factors associated with activation of the SNS and other demographic risk factors, genetic variations among individuals have also been shown to be predictive risk factors for the development of dementia, such as Alzheimer's disease, in later life. For example, early-onset familial Alzheimer's disease (EOFAD) is inherited in an autosomal dominant manner. Carriers of particular heritable polymorphisms in the genes encoding for amyloid-β protein precursor (AβPP), presenilin 1, and presenilin 2 are known to cause EOFAD (Frost, S., et al., *J Alzheimers Dis*, 2010, 22: 1-16). Sporadic Alzheimer's disease has been associated with the apolipoprotein E genotype, APOE ε4, implicated in modulating the metabolism and aggregation of β-amyloid peptides (Frost, S., et al., *J Alzheimers Dis*, 2010, 22: 1-16; Kivipelto, M., et al. *Lancet Neurol*, 2006, 5: 735-741). For example, a carrier of a single copy of the APOE ε4 allele has a 2-3 fold increased risk of developing Alzheimer's disease in later life, and two copies of the allele increases the risk 12 fold (Frost, S., et al., *J Alzheimers Dis*, 2010, 22: 1-16). Additionally, genetic association studies have linked genetic polymorphisms of Clusterin, phosphatidylinositol binding clathrin assembly protein (PICALM) and complement receptor 1 (CR1) genes to an increased likelihood of developing Alzheimer's disease (Id.). One of ordinary skill in the art of genetic profiling techniques will appreciate that additional genes having an effect on dementia risk, including Alzheimer's risk, may prove useful in providing diagnostic markers for individuals having an increased risk of developing dementia in later life.

No effective treatments currently exist to reverse progression of dementia. Certain approved drug therapies that may provide modest benefit to Alzheimer's disease patients include, for example, cholinesterase inhibitors (e.g., available under the trade names Aricept®, Exelon® Patch, and Razadyne®) that boost levels of acetylcholine, which is involved in memory and judgment, and memantine (available under the trade name Namenda®) which regulates glutamate, which is important for information processing, storage, and retrieval. Recommended medical protocols for the prevention (e.g., risk reduction) of dementia include lifestyle recommendations (e.g., don't smoke, eat healthy diet, exercise, etc.) as well as disease management (e.g., maintain blood pressure within recommended limits, cholesterol reduction/maintenance). Often physicians will administer medications to accomplish these goals. For example, patients having high blood pressure will be prescribed anti-hypertensive drugs. However, drug adherence over several years or decades in a manner that maintains blood pressure remains a challenge for most patients. Additional drawbacks to use of anti-hypertensive drugs for treating a patient include the possibilities of adverse reactions associated with β-adrenoreceptor blockade (e.g., heart failure, hypotension, bradycardia, depression, insomnia, sexual dysfunction, etc.), risks associated with β-blocker intoxication (e.g., death), and management of contraindications (e.g., concomitant use with α1-adrenergic antagonists, calcium channel blockers, and other pharmaceutical cardiovascular interventions) on a patient-by-patient basis. Additionally, pharmaceutical intervention for other contributors and risk factors associated with development of dementia further complicates drug administration and management of contraindications between anti-inflammatory medications, anti-hypertensive drugs, antidepressant drugs, and acetylcholinesterase inhibitors, among others administered to support dementia patients. Moreover, adherence over years remains a challenge. Various aspects of the present technology address SNS effects on risk factors associated with dementia while overcoming these challenges.

C. Identification of Patients or Cohorts at Risk of Developing Dementia

Patients presenting a high or increased risk of developing dementia can include patients presenting with hypertension or pre-hypertension, patients presenting with 24-hour blood pressure variability, patients with above-normal cholesterol levels, patients diagnosed with atherosclerosis, patients with history of smoking, patients presenting with elevated serum inflammatory cytokine levels, patients presenting with insulin resistance or other metabolic disorders, patients having had a stroke (e.g., acute ischemic stroke, lacunar stroke, TIA, hemorrhagic stroke, etc.), patients diagnosed with arterial stiffening or aneurysm(s), patients presenting with unexplained vision loss, patients having a family history of dementia (e.g., Alzheimer's disease), patients who are over-weight or clinically obese, and/or sedentary patients with or without other high risk factors. In some embodiments, the patient can be normotensive and present one or more risk factors. In certain embodiments, the patient can be middle-aged (e.g., 45-65) and present with one or more risk factors.

In some embodiments of the present technology, the patient can be middle-aged and have a calculated risk score for the prediction of dementia risk in later life that is above a threshold dementia risk score. Such a calculated dementia risk score can indicate a likelihood of developing dementia within a particular time frame (e.g., within 10 years, within 20 years, etc.). In one embodiment, for example, a calculated risk score for the prediction of developing dementia in later life can be based upon one or more data sets known in the art. For example, a dementia risk score based upon the population-based Cardiovascular Risk Factors, Aging, and Dementia (CAIDE) study, which included 1409 individuals who were studied in midlife and re-examined 20 years later for signs of dementia, can be used to establish a dementia risk score or a percent probability of developing dementia in 20 years (Kivipelto, M., et al. *Lancet Neurol*, 2006, 5: 735-741). The dementia risk score can be based upon an analysis of the patient's assessment across multiple possible risk factors. One of ordinary skill in the art will recognize that the CAIDE study is only one study in which a risk score calculation can be developed and applied. For example, other published data sources documenting multiple possible risk factors and corresponding scores may use any of many well described techniques. Such techniques for developing tools to calculate a dementia risk score could be empirical, based on multivariate regression, or using artificial intelligence (e.g. Bayesian probability, machine learning, etc.) among other techniques known in the art.

As discussed above, genetic variances can constitute dementia predictors or risk factors in certain patients. For example, a patient presenting a high or increased risk of developing dementia can have a genetic disorder or determined genetic pre-disposition to developing dementia. In a particular example, a specific form of the apolipoprotein E gene, APOE-ε4, is linked to Alzheimer's disease. A genetic predisposition may also cause the early onset of cognitive decline, and in some cases present a high risk of developing early onset dementia (e.g., EOFAD). For example, particular mutations in AβPP, presenilin 1 and presenilin 2 can be used as genetic biomarkers for identifying such at risk patients.

A patient suspected of having cognitive decline or impairment or having one or more specific forms of dementia, can be evaluated for a level of dysfunction or severity of cognitive impairment. Evaluation of cognitive function can include a self-reporting or assessment of changes from a person's usual level of function, such as the patient's ability to function independently or perform daily activities (e.g., dressing, bathing, meal preparation). Evaluation input may also come from trusted sources (e.g., trusted family members, friends, primary physician, etc.) that can provide information on changes in performance of daily activities, job/employment performance, behavior or mood changes, etc.

Physicians may also administer one or more brain functioning tests to assess a state of brain function in executive function (e.g., Controlled Oral Word Association Test, Category Fluency Test, Trail Making Test Part B, etc.), brain processing speed (e.g., Digital Symbol Substitution test, Trail Making Test Part A, etc.), and/or memory function (e.g., Digits Forward Test, first trial of the Rey Auditory Learning Test, etc.). Evaluation of brain function by cognitive testing may also include administering the Alzheimer's Disease Assessment Scale-Cognitive Subscale test, Mini-Mental State Examination (MMSE) and/or the Cambridge Cognitive Examination (CAMCOG). One of ordinary skill in the art will recognize other cognitive tests and scales that can be used to determine a state of brain function (e.g., executive function, processing speed, memory function, etc.) in a patient. In some embodiments, a patient may be suspected of having cognitive decline or impairment based upon a single test score, combined test scores from multiple tests, or one or more test scores from multiple tests. Diagnosis can be made based upon, for example, receiving one or more scores that are below a threshold test score (e.g., failing to pass one or more portions of a test). In other embodiments, a patient may demonstrate a decline in test scores over time. For example, a particular patient may show a drop in a test score between taking tests 6 months apart, a year apart, or in other embodiments, 2, 3, 4, 5 or more years apart. Cognitive functioning, as well as other data that can be collected in an evaluation of a patient, are based on self-reporting, observational (behavioral), or psychological data.

In addition to self-reporting, observational or other psychological data, a patient may also be evaluated for physiological data. Accordingly, a patient may demonstrate one or more physiological parameters associated with vascular cognitive impairment, Alzheimer's disease or another form of dementia. Non-limiting examples of physiological parameters may include determination of atherosclerosis of extracranial and/or intracranial arteries (e.g., as assessed by CT scan, cerebral angiography, etc.), or clinical measurements of aortic and large-artery stiffening (e.g., as assessed by pulse wave velocity (PWV), augmentation index, etc.), which can be good predictors of vascular remodeling and stiffening in the cerebral arteries and arterioles and narrowing of arteriole lumens. Other examples of physiological parameters associated with vascular cognitive impairment may include small-vessel disease or other alterations in small arteries supplying the subcortical and basal ganglia white matter leading from the base of the brain, a reduction in cerebral blood flow (e.g., loss of microvessels), blood-brain barrier disruption (e.g., as assessed by MRI), white matter lesions (e.g., as assessed by MRI), brain imaging evidence of recent stroke (e.g., acute ischemic stroke, lacunar stroke, TIA, hemorrhagic stroke, etc.), brain imaging evidence for detection of Lewy bodies, or brain imaging confirmation of Alzheimer's disease (e.g., progressive cerebral atrophy, blood oxygen level-dependent (BOLD) MR signal). For example, reduction in hippocampal volume (e.g., as assessed by MRI) may be used as a biomarker for the early detection of Alzheimer's disease (Frost, S., et al., *J Alzheimers Dis*, 2010, 22: 1-16).

Brain imaging evidence can include, for example, brain CT, structural and functional MRI, and positron emission tomography (PET; for assessment of both cerebral metabolism and amyloid) with fluoro-deoxy-D-glucose (FDG) and amyloid tracers (Johnson, K. A., et al., *Cold Spring Harb Perspect Med*, 2012, 2:a006213). In addition to measuring structural changes (e.g., cerebral atrophy, hippocampal volume reduction, etc.), functional MRI can be used to detect changes to brain function (e.g., neural activation) (Frost, S., et al., *J Alzheimers Dis*, 2010, 22: 1-16). Additional biomarkers for the early detection of Alzheimer's disease can include, for example, changes in cerebral spinal fluid concentrations of specific longer peptides of β-amyloid associated with Alzheimer's plaques or in tau protein (Id.).

Some forms of dementia (e.g., Alzheimer's disease) are associated with ocular abnormalities and vision changes. For example, patients presenting with Alzheimer's disease are reported as having altered ocular morphologies and/or properties including, for example, a hypersensitive pupil response to cholinergic drops (e.g., during ophthalmological examination), altered pupil light reflex (e.g., response of the pupil to a bright flash of light), the presence of equatorial supranuclear cataracts (e.g., as visualized by slit-lamp microscopy) possibly via the presence of β-amyloid aggregation in the lens of the eye, abnormalities and/or cell loss of the retinal nerve fiber layer (e.g., as visualized/measured by optical coherence tomography; as demonstrated by abnormal pattern electroretinogram), narrower retinal veins and/or decreased venular blood flow (e.g., as measured by laser Doppler), and optic disc changes (e.g., optic disc pallor, disc cupping, thinning of the neuro-retinal rim, etc.) (Frost, S., et al., *J Alzheimers Dis*, 2010, 22: 1-16). Alzheimer's disease-related changes in the eye may occur prior to the patient experiencing symptoms relating to cognitive decline associated with this neurological disorder. In particular, the presence of one or more Alzheimer's disease-related optical properties may function as a non-invasive and/or simple biomarker for identifying patients at risk of developing dementia and/or in early stages of dementia (Id.). In accordance with particular embodiments, patients presenting one or more optical morphologies and/or properties associated with Alzheimer's disease, either prior to or following experiencing symptoms associated with cognitive decline, can be candidates for treatment using renal neuromodulation.

As discussed above, individuals at risk of having a stroke (e.g., acute ischemic stroke, lacunar stroke, transient ischemic attack (TIA), hemorrhagic stroke, etc.) or having a history of having one or more strokes, have an increased risk of developing dementia later in life (Iadecola, C., et al., *Hypertension*, 2016, 68: e67-e94). Accordingly, patients having increased risk of stroke or history of stroke, irrespective of blood pressure level, can be treated with renal neuromodulation to improve neurological function, provide protection of neurological function and/or prevent future cognitive decline in these at-risk patients (Hasegawa, Y., et al., *Stroke*, 2017, doi: 10.1161/STROKEAHA.116.015782).

In accordance with aspects of the present technology, patients presenting with one or more risk factors for developing dementia and/or having a calculated dementia risk score above a threshold dementia risk score can be candidates for treatment for the prevention of dementia in later life. As noted above, renal neuromodulation is expected to efficaciously prevent an incidence of, reduce a severity of, or slow a progression of one or more forms of dementia, such as vascular dementia or Alzheimer's disease. In other embodiments, renal neuromodulation is expected to therapeutically prevent an incidence of, reduce a severity of, or prevent a progression to dementia from mild cognitive impairment. Renal neuromodulation is further expected to improve a patient's calculated risk score of developing dementia. In certain embodiments, renal neuromodulation treats several clinical conditions characterized by increased overall sympathetic activity, and, in particular, conditions associated with central sympathetic overstimulation such as pre-hypertension, hypertension, blood pressure variability, vascular disease (e.g., vessel stiffening), metabolic syndrome, insulin resistance, diabetes, and systemic inflammation, among others, that may be associated with and/or contribute to a risk of developing dementia. The reduction of afferent neural signals typically contributes to the systemic reduction of sympathetic tone/drive, and renal neuromodulation is expected to be useful in treating several conditions associated with systemic sympathetic overactivity or hyperactivity.

II. RENAL NEUROMODULATION FOR REDUCING A RISK ASSOCIATED WITH THE DEVELOPMENT OF DEMENTIA

While sympathetic drive regulation can have adaptive utility in maintaining homeostasis or in preparing many organs in the body for a rapid response to environmental factors, chronic activation of the SNS (e.g., associated with primary aging, age-associated obesity, chronic stress, etc.) is a common maladaptive response that can contribute to certain diseases and conditions (e.g., hypertension, systemic or localized inflammation, vascular remodeling, atherosclerosis, obesity, insulin resistance, etc.). These diseases and conditions can, in turn, increase a patient's risk of developing dementia and/or drive progression and/or severity of dementia in a patient. Excessive activation of the renal SNS in particular has been identified experimentally and in humans as a likely contributor to the complex pathophysiology of hypertension, states of volume overload (such as heart failure), and progressive renal disease. As examples, radiotracer dilution has demonstrated increased renal norepinephrine spillover rates in patients with essential hypertension.

Aspects of the present disclosure include targeting renal SNS nerve fibers for neuromodulation in patients (1) having an increased risk associated with developing dementia, (2) having been diagnosed with mild cognitive impairment, and/or (3) demonstrating one more physiological and/or psychological symptoms associated with dementia. Targeting renal SNS nerve fibers for neuromodulation in patients can effectively attenuate neural traffic along the sympathetic nerves. Without being bound by theory, attenuation of neural traffic along renal sympathetic nerves can be used, for example, to treat or prohibit deleterious vascular changes associated with dementia, decrease systemic inflammatory responses associated with dementia, and/or decrease a progression rate or level of severity of dementia.

In one example, renal sympathetic neuromodulation can be used to reduce a patient's systolic blood pressure. In another example, renal sympathetic neuromodulation can be used to decrease 24-hour blood pressure variability in a patient. In other embodiments, attenuation of neural traffic along renal sympathetic nerves can be used to treat or prevent metabolic disorders, obesity and/or insulin resistance in the patient having an increased risk associated with developing dementia. In yet a further embodiment, renal sympathetic neuromodulation can be used to lower one or more levels of inflammatory biomarkers in a patient. Some of the effects of chronic SNS activation take place prior to any noticeable signs or symptoms associated with a decline in cognitive abilities. Additionally, the effects of chronic SNS activation can cause unseen damage to brain tissue and/or vascular tissue prior to the appearance of quantifiable disease indicators typically associated with dementia progression. For example, chronic SNS activation during middle-age (e.g., 45-65 years old) can alter vascular tissue (e.g., weaken vessel walls, contribute to hardening of the arteries, cause inflammatory vessel damage) or place burden on other physiological systems causing risk-increasing disorders (e.g., insulin resistance and other metabolic disorders) that may increase the patient's risk of developing dementia later in life (e.g., within 10 years, within 15 years, within 20 years, etc.). In one embodiment, neuromodulation treatment can be used to treat patients having a high risk of developing dementia (e.g., having a dementia risk score above a threshold dementia risk score, having one or more dementia risk factors, having a combination of dementia risk factors, etc.) to reduce a) systemic plasma levels of norepinephrine from, e.g., spillover from innervation of smooth muscle surrounding blood vessels, b) systemic plasma levels of inflammatory biomarkers (e.g., IL-6, CRP, etc.), and/or c) high blood pressure.

In one embodiment, a patient demonstrating a mild cognitive decline or other indicators, such as pre-hypertension (e.g., systolic BP of 120-139 mmHg/diastolic BP of 80-89 mmHg), hypertension (e.g., systolic BP >140 mmHg/diastolic BP >90 mmHg), increased serum levels of IL-6 or CRP, atherosclerosis and/or above normal cholesterol levels, arterial stiffening, small-vessel disease, previous stroke (e.g., acute ischemic stroke, lacunar stroke, TIA, hemorrhagic stroke, etc.), or having other factors presenting an increased risk of developing dementia (e.g., persons having familial history of dementia, APOE ε4 carrier) can be treated with renal neuromodulation to reduce a level of renal sympathetic drive and/or reduce a level of systemic norepinephrine spillover in circulating plasma (Schlaich, M. P., et al., Frontiers in Physiology, 2012, 3(10): 1-7).

In some embodiments, a patient demonstrating mild cognitive decline can be diagnosed with mild cognitive impairment by a physician. In other embodiments, a patient demonstrating mild cognitive decline can present with a lower performance result on a brain functioning test (e.g., test for executive function, processing speed and/or memory function). In further embodiments, mild cognitive decline can refer to patients diagnosed with early stage dementia. Accordingly, patients may be treated with renal neuromodulation to prevent an onset of dementia, reduce a risk factor score associated with the development of dementia, slow a progression of dementia, or reduce a severity of dementia.

Several embodiments of the present technology utilize intravascular devices that reduce sympathetic nerve activity by applying, for example, radiofrequency (RF) energy to target nerve(s) and/or other target site(s) in patients presenting one or more physiological symptoms associated with vascular cognitive impairment or other form of dementia, or having a risk of developing dementia, such as having a risk score above a threshold level. In certain embodiments, neuromodulation is used to reduce renal sympathetic nerve activity in patients having a high risk (e.g., a predisposition or increased likelihood) of developing dementia, one or more signs or symptoms associated with mild cognitive impairment, or, in further embodiments, in patients having been diagnosed with a form of dementia.

Renal neuromodulation is the partial or complete incapacitation or other effective disruption of the nerves of the kidneys, including nerves terminating in the kidneys or in structures closely associated with the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for preventing incidence of various forms of dementia (e.g., vascular cognitive impairment, Alzheimer's disease, etc.), for slowing progression of dementia, reducing a severity of dementia, or for alleviating symptoms and other sequelae associated with dementia over longer periods of time, short-term modulation of the renal nerves may also be desirable. For example, some patients may benefit from short-term modulation to address acute symptoms of dementia, such as anxiety, insomnia, mood swings, or other transitional behavioral changes. In particular, some patients may benefit from short-term modulation to address the effects of dementia progression, such as adjuvant therapy to increase effectiveness of co-administered drugs (e.g., anti-inflammatory medications, anti-hypertensive drugs, antidepressant drugs, acetylcholinesterase inhibitors among others administered to support dementia patients).

Figure 2:
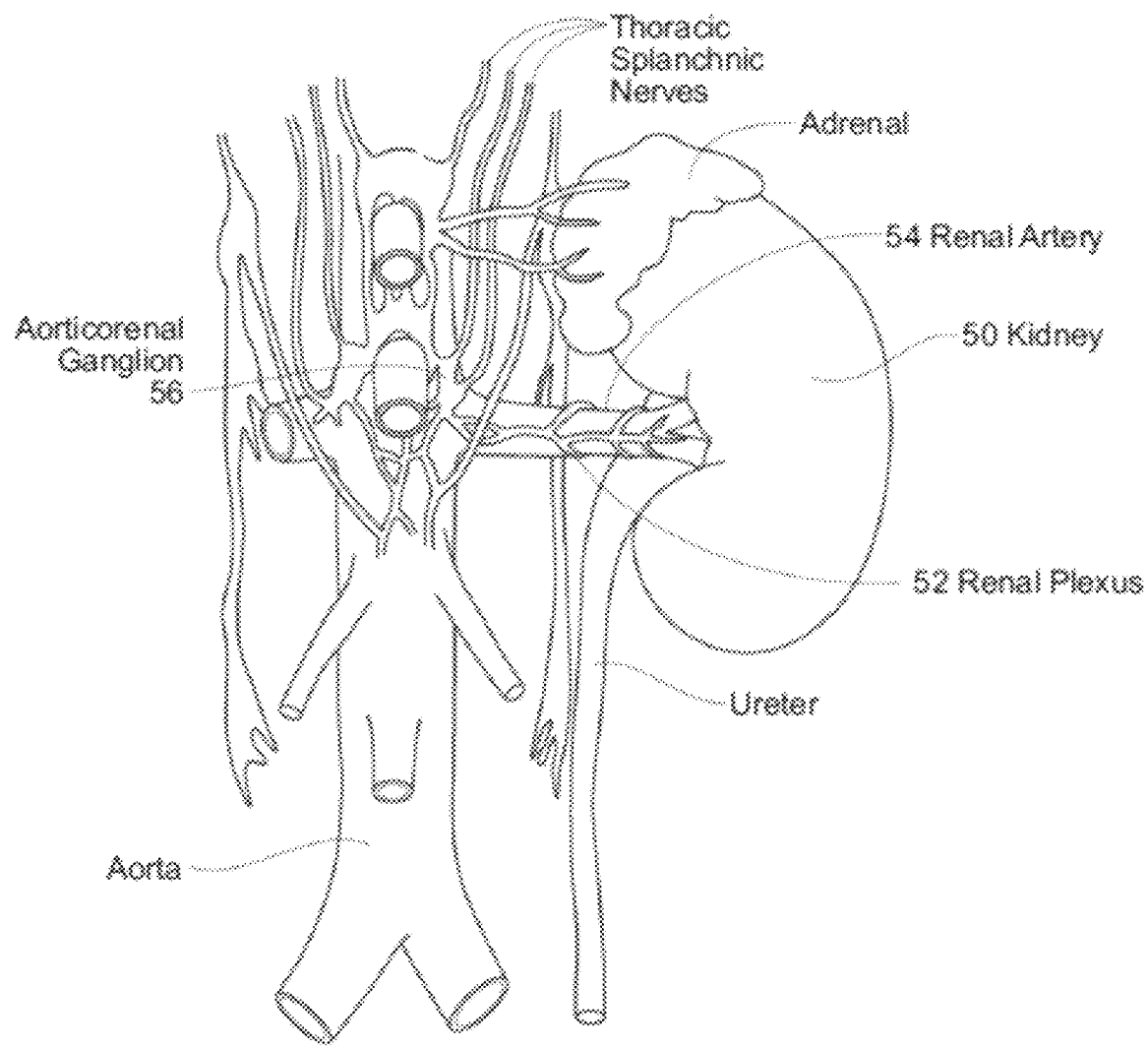
FIG. 2 is an enlarged anatomic view of nerves of a left kidney to form the renal plexus surrounding the left renal artery.

FIG. 2 is an enlarged anatomic view of nerves innervating a left kidney 50 of a patient. As FIG. 2 shows, the kidney 50 is innervated by a renal plexus 52, which is intimately associated with a renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50, innervating the kidney while terminating in the blood vessels, the juxtaglomerular apparatus, and the renal tubules (not shown). Fibers contributing to the renal plexus 52 arise from the celiac ganglion (not shown), the superior mesenteric ganglion (not shown), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord (renal sympathetic nerves arise from T10-L2, FIG. 1). Referring to FIGS. 1 and 2 together, preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion (FIG. 1), the superior mesenteric ganglion (FIG. 1), and the aorticorenal ganglion 56. Postganglionic neuronal cell bodies exit the celiac ganglion, the superior mesenteric ganglion, and the aorticorenal ganglion 56 to the renal plexus 52 and are distributed to the renal vasculature.

It has previously been shown that stimulation of renal efferent nerves directly affects neural regulation components of renal function that are considerably stimulated in disease states characterized by heightened sympathetic tone such as, for example, increased blood pressure in hypertensive patients. As provided herein, renal neuromodulation is likely to be valuable in the treatment of diseases and conditions that are associated with increased risk of developing dementia such as, for example, hypertension, increased blood pressure variability, systemic inflammation, vascular inflammation, vessel remodeling and/or hardening, atherosclerosis, and metabolic disorders among others. In particular, renal neuromodulation along the renal artery and/or within branches of the renal artery as described in U.S. patent application Ser. No. 14/839,893, filed Aug. 28, 2015 and incorporated herein by reference in its entirety, is expected to reduce renal sympathetic drive in the kidney, thereby reducing the negative impact of SNS activation on aspects of these and other conditions associated with physiological changes that have impact on brain health. As such, renal neuromodulation is also likely to be particularly valuable in patients having one or more clinical conditions characterized by increased overall and particularly renal sympathetic activity, such as hypertension, increased blood pressure variability, systemic inflammation, chronic vascular inflammation, metabolic syndrome, insulin resistance and diabetes, among others.

As the reduction of afferent neural signals contributes to the systemic reduction of sympathetic tone/drive, renal neuromodulation might also be useful in treating dementia, particularly early stage dementia. For example, a reduction in central sympathetic drive may reduce and/or improve measurable physiological parameters associated with the progression of dementia, such as increasing blood flow to the brain, reducing cerebrovascular inflammation, reducing disruption of the blood-brain barrier, reducing risk of stroke (e.g., acute ischemic stroke, lacunar stroke, TIA, hemorrhagic stroke, etc.), and/or other cardiovascular events. In other embodiments, reducing sympathetic neural activity in the renal nerve and/or reducing central sympathetic drive can include improving an effectiveness of a dementia drug (e.g., cholinesterase inhibitors, memantine), or other pharmaceutical intervention (e.g., anti-inflammatory drug, antihypertensive drug, etc.) in the patient.

In accordance with several aspects of the present technology, renal neuromodulation is used for the prevention or treatment of several forms of dementia. Non-limiting examples of forms of dementia that may be prevented or treated using renal neuromodulation of targeted SNS neural fibers include Alzheimer's disease, vascular cognitive impairment (e.g., vascular dementia, cerebrovascular diseases), dementia with Lewy bodies, and mixed dementia. Additional examples of dementia may include, but are not limited to, dementia associated with Parkinson's disease, frontotemporal dementia (behavioral variant frontotemporal dementia, primary progressive aphasia, Pick's disease, corticobasal degeneration, and progressive supranuclear palsy), Creutzfeldt-Jakob disease, normal pressure hydrocephalus, Hunting's disease and Wernicke-Korsakoff Syndrome.

Intravascular devices that reduce sympathetic nerve activity by applying, for example, RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent RAAS activation) and sodium retention and decreased renal blood flow. These neural regulation components of renal function are considerably stimulated in disease states characterized by heightened sympathetic tone and likely contribute to increased blood pressure in hypertensive patients and increased levels of peripheral inflammatory markers, such as IL-6 and CRP, in patients experiencing a host of inflammatory challenges including chronic vascular inflammation (Dörr, O. et al., *Clin Res Cardiol*, 2015, 104: 175-184). The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure).

Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radio frequency (RF) ablation) have been shown to reduce blood pressure, decrease blood pressure variability, improve arterial stiffness and reduce mediators of systemic inflammation in patients with treatment-resistant hypertension (Dörr, O., et al., *Clin Res Cardiol*, 2015, 104: 175-184; Zuern, C. S., et al., *Front. Physiol*, 2012, 3(134): 1-8; Baroni, M., et al., *High Blood Press Cardiovasc Prev*, 2015, (4):411-6; Brandt, M. C., et al., *JACC*, 2012, 60(19): 1956-65; Mortensen, K., et al., *J Clin Hypertens*, 2012, 14(12): 861-870).

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of a renal blood vessel (e.g., renal artery, renal arterial branch, renal ostium, renal vein) and adjacent regions of the renal plexus RP, which lay intimately within or adjacent to the adventitia of the renal blood vessel. Some embodiments of the present technology, for example, include electrode-based or transducer-based approaches, which can be used for therapeutically-effective neuromodulation. For example, an energy delivery element (e.g., electrode) can be configured to deliver electrical and/or thermal energy at a treatment site.

By way of theory, targeting both general afferent and efferent renal sympathetic nerves (e.g., via a catheter-based approach, extracorporeal ultrasound, etc.) may cause beneficial effects extending well beyond affecting a risk associated with developing dementia and/or dementia progression in a patient, such as reducing a risk of stroke, cardiovascular disease and/or other end organ damage. As discussed herein, a correlation between age-related vascular alterations and hypertension and an increased risk of developing cognitive impairment, including debilitating cognitive impairment associated with dementia, has been implicated. There is now also evidence that dementia and age-related cognitive decline is associated with chronic inflammatory responses and age-related sympathetic activation appears to affect serum levels of peripheral inflammatory markers. Additionally, chronic stress, obesity and other cardiovascular maladies promote hyperactivity (e.g., overactivity) of the sympathetic nervous system throughout the body. For example, when experiencing stress, including chronic stress, hormonal and neural information (e.g., sensory afferent input) is received by the CNS, which in turn further elevates sympathetic tone via efferent signaling throughout the body. Some aspects of methods of treating patients having one or more risk factors, including a high risk score, for the development of dementia using sympathetic neuromodulation are at least in part derived from the recognition described herein that the kidneys may contribute to elevated central sympathetic drive.

Several aspects of the current technology are configured to reduce renal sympathetic nerve activity within or near the kidney(s) to reduce localized release of norepinephrine. Several properties of the renal vasculature may inform the design of treatment devices and associated methods for achieving target sympathetic neuromodulation, for example, via intravascular access, and impose specific design requirements for such devices. Specific design requirements for renal neuromodulation may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively modulating the renal nerves with the neuromodulatory apparatus.

Intravascular devices that reduce sympathetic nerve activity by applying, for example, RF energy to a treatment site in the renal artery have recently been shown to reduce renal sympathetic drive, renal norepinephrine spillover, and whole body norepinephrine spillover. Renal neuromodulation is expected to reduce renal sympathetic neural activity, and since the reduction of afferent neural signals contributes to the systemic reduction of sympathetic tone/drive, renal neuromodulation is a useful technique in addressing certain risk factors associated with developing dementia that are attributable to systemic sympathetic hyperactivity. For example, as previously discussed, a reduction in central sympathetic drive may reduce a likelihood of developing dementia or other milder age-related cognitive decline, as well as improve other disease manifestations (e.g., hypertension, metabolic disorders, insulin resistance, diabetes, systemic inflammation, etc.) associated with sympathetic hyperactivity.

Accordingly, renal neuromodulation is expected to be useful in preventing an incidence of developing dementia in patients presenting certain risk factors, or in slowing a progression of dementia/cognitive decline and/or reduce a severity of dementia in afflicted patients. The beneficial effect of renal neuromodulation with respect to a risk associated with development of cognitive decline or dementia is expected to apply to middle-aged patients (e.g., about 45-65 years old, about 50-65 years old, about 50-60 years old, etc.), for example, regardless of the baseline renal sympathetic neural activity or the baseline level of norepinephrine in plasma (e.g., whole body norepinephrine spillover). For example, renal neuromodulation in accordance with embodiments of the present technology can improve one or more measurable physiological parameters corresponding to a dementia risk factor in the middle-aged patient when baseline renal sympathetic neural activity is normal, below normal, or above normal (e.g., hyperactive or overactive). Likewise, renal neuromodulation in accordance with additional embodiments of the present technology can improve one or more measurable physiological parameters corresponding to a dementia risk factor in the middle-aged patient when baseline central sympathetic drive, baseline norepinephrine spillover in plasma, and/or whole body norepinephrine spillover is normal, below normal, or above normal (e.g., hyperactive or overactive). Such an improvement in one or more measurable physiological parameters corresponding to a dementia risk factor in the middle-aged patient can reduce a risk associated with developing dementia in that patient at older age (e.g., about 65-85 years old, greater than about 60 years old, greater than about 65 years old, greater than about 70 years old, greater than about 75 years old, etc.).

III. METHODS FOR REDUCING A RISK ASSOCIATED WITH DEVELOPING DEMENTIA AND RELATED CONDITIONS

Disclosed herein are several embodiments of methods directed to preventing an incidence of dementia and other conditions associated with an increased risk of developing cognitive impairment in a patient using catheter-based renal neuromodulation. Further embodiments disclosed herein are directed to treatment of effects associated with vascular cognitive impairment and other forms of dementia using renal neuromodulation. The methods disclosed herein may represent various advantages over a number of conventional approaches and techniques in that they allow for the potential targeting of elevated sympathetic drive, which may either be a cause of several vascular and other cognitive risk factors associated with dementia or a key mediator of disease progress. Also, the disclosed methods provide for localized treatment and limited duration treatment regimens (e.g., one-time treatment), thereby reducing patient long-term treatment compliance issues.

In certain embodiments, the methods provided herein comprise performing renal neuromodulation, thereby decreasing sympathetic renal nerve activity, for example, for the purposes of being able to provide one or more of a reduction in a number of dementia risk factors, a reduction in severity of one or more dementia risk factors, a reversal in vascular damage facilitated by sympathetic activity, a reduction in systemic inflammation, or a reduction in a calculated dementia risk score. For example, renal neuromodulation is expected to reduce a level of central sympathetic activity that may contribute to one more underlying causes of dementia.

Renal neuromodulation may be repeated one or more times at various intervals until a desired sympathetic nerve activity level or another therapeutic benchmark is reached. In one embodiment, for example, a decrease in sympathetic nerve activity may be observed via a marker of sympathetic nerve activity in patients, such as decreased levels of plasma norepinephrine (noradrenaline), changes in levels of systemic renin in plasma, and/or changes in levels of systemic aldosterone in plasma. Other measures or markers of sympathetic nerve activity can include muscle sympathetic nerve activity (MSNA), norepinephrine spillover, and/or heart rate variability. In another embodiment, other measurable physiological parameters or markers, such as improved blood pressure control (lower blood pressure, reduced blood pressure variability), lower levels of peripheral inflammatory biomarkers (e.g., IL-6, CRP, etc.), changes in aldosterone-to-renin ratio (ARR), changes in a salt suppression test, changes in blood plasma levels of potassium, improved blood glucose regulation, etc., can be used to assess efficacy of the thermal modulation treatment for patients having one or more risk factors for developing dementia, having a calculated dementia risk score above a threshold dementia risk score, having developed mild cognitive impairment, and/or diagnosed as early stage dementia. In certain embodiments, renal neuromodulation may be repeated one or more times at various intervals until a desired sympathetic nerve activity level or another therapeutic benchmark is reached for such patients.

In certain embodiments of the methods provided herein, renal neuromodulation is expected to result in a change in sympathetic nerve activity and/or in other measurable physiological parameters or markers, over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment.

A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months, 12 months or 24 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

In one embodiment, measured norepinephrine content (e.g., assessed via tissue biopsy, assessed in real-time via intravascular blood collection techniques, etc.) can be reduced (e.g., at least about 5%, 10%, 20% or by at least 40%) in the patient within about three months after at least partially inhibiting sympathetic neural activity in nerves proximate a renal blood vessel.

In one embodiment, renal sympathetic neuromodulation may be performed on a patient having one or more risk factors associated with developing dementia to improve the physiological state of at least one of the dementia risk factors. In some embodiments, for example, renal sympathetic neuromodulation may reduce blood pressure, reduce blood pressure variability, reduce a serum level of an inflammatory biomarker, or reduce a level of insulin resistance. A reduction in blood pressure can be, for example, by at least about 5%, 10%, or a greater amount as determined by average blood pressure analysis before and after (e.g., 1, 3, 6, or 12 months after) a renal neuromodulation procedure. In a particular example, a pre-hypertensive patient (e.g., systolic BP of 120-139 mmHg/diastolic BP of 80-89 mmHg) may have blood pressure below the pre-hypertensive range after a renal neuromodulation procedure. Likewise, a hypertensive patient (e.g., systolic BP >140 mmHg/diastolic BP >90 mmHg) may have blood pressure below the hypertensive range after a renal neuromodulation procedure. Corresponding results may be obtained with plasma aldosterone concentration, plasma renin activity, and/or aldosterone-to-renin ratio. For example, a reduction in an aldosterone-to-renin ratio can be, for example, by at least about 5%, 10% or a greater amount (e.g., about 50%, about 80%, about 90%) as determined by blood analysis and calculation before and after (e.g., 1, 3, 6, or 12 months after) a renal neuromodulation procedure.

In the case of systemic inflammation and/or a patient having elevated serum levels of inflammatory biomarkers, IL-6 and CRP, renal sympathetic neuromodulation may improve (e.g., reduce a level of) markers of inflammation (e.g., IL-6, CRP), and in some embodiments, provide a reduction in IL-6 and/or CRP, for example, by about 5%, 10%, 25%, 45% or a greater amount as determined by blood analysis before and after (e.g., 1, 3, 6, or 12 months after) a renal neuromodulation procedure. In other embodiments, renal sympathetic neuromodulation may increase arteriole blood flow, reduce a level of atherosclerosis, or reduce a degree of arterial stiffening in the patient by about 5%, 10% or a greater amount as determined by qualitative or quantitative analysis (e.g., CT scan, PWV analysis, angiography, etc.) before and after (e.g., 1, 3, 6, or 12 months after) a renal neuromodulation procedure.

In another embodiment, renal sympathetic neuromodulation may be performed on a patient having a calculated dementia risk score above a threshold dementia risk score to improve the patient's dementia risk score and thereby reduce the probability that the patient will develop dementia in later life (e.g., within about 5 years, about 10 years, about 20 years, etc.). In one embodiment, a threshold dementia risk score may be a theoretical risk score (e.g., based on population studies) that represents an upper limit of acceptable risk of dementia in later life. For example, a patient may be assessed for a number of factors that have been previously determined to carry risk for the development of dementia (e.g., age, education, gender, blood pressure, body mass index, cholesterol levels, smoking habits, weekly activity levels, etc.). Using a dementia risk score calculator tool (e.g., based on epidemiological data), a patient's risk score can be assessed. For patients having a calculated dementia risk score above the threshold dementia risk score (e.g., signifying an undesirable dementia probability in about 5 years, about 10 years, about 20 years, etc.), a renal sympathetic neuromodulation procedure is performed. Renal neuromodulation may improve (e.g., lower, reduce a rate of increase over time, etc.) the patient's dementia risk score. For example, following a renal neuromodulation procedure, a patient's calculated dementia risk score may reduce (e.g., improve) by about by about 5%, 10%, 15%, 20%, 25%, 30%, 40%, 45% or a greater amount as determined by the dementia risk score calculator tool. Such improvements in a patient's dementia risk score may be detected, for example 1, 3, 6, or 12 months after a renal neuromodulation procedure.

In addition to (or instead of) affecting one or more measurable risk factors associated with the development of dementia, renal sympathetic neuromodulation may efficaciously treat one or more measurable physiological parameter(s) or sequela(e) corresponding to the progression of cognitive decline in the patient. For example, in some embodiments, renal neuromodulation may result in an improvement (e.g., prevent further decline, maintain, or improve) in a patient's cognitive abilities as assessed by one or more brain functioning tests (e.g., Alzheimer's Disease Assessment Scale-Cognitive Subscale test, MMSE, CAM-COG, executive function tests, brain processing speed tests, memory function tests, etc.). In a specific embodiment, a patient may improve a brain functioning test score, maintain a brain functioning test score, or decrease a rate of decline in a test score over time following a renal neuromodulation procedure. Such improvements in a patient's cognitive abilities may be detected, for example 1, 3, 6, or 12 months after a renal neuromodulation procedure. In other embodiments, improvements are detected 2, 3, 4, 5 or 10 years after a renal neuromodulation procedure. In some embodiments, a test score can be increased by about 5%, about 10%, about 15%, about 20%, about 30%, about 40%, about 50%, or about 75%. In other embodiments, patients may report that daily activities are easier following a neuromodulation procedure.

In a patient at risk of having a stroke (e.g., acute ischemic stroke, lacunar stroke, TIA, hemorrhagic stroke, etc.) or having a history of having one or more strokes, the patient may have an improvement in neurological function following a renal neuromodulation procedure as determined by one or more brain functioning tests (e.g., Alzheimer's Disease Assessment Scale-Cognitive Subscale test, MMSE, CAM-COG, executive function tests, brain processing speed tests, memory function tests, etc.) or, in other embodiments, by functional MRI measurement of neural brain activity before and after (e.g., 1, 3, 6, or 12 months after; 2, 3, 4, 5 or 10 years after) the renal neuromodulation procedure. In some embodiments, a test score can be increased by about 5%, about 10%, about 15%, about 20%, about 30%, about 40%, about 50%, or about 75%. In other embodiments, neural brain activity, as measured by functional MRI, can increase by about 5%, about 10%, about 15%, about 20%, about 30%, or about 40% or greater.

Other measurable physiological parameters may also improve following renal sympathetic neuromodulation. For example, a patient may have an improvement in (e.g., reduction, maintain a level of, slow a rate of progression of) at least one of atherosclerosis of extracranial and/or intracranial arteries, clinical measurements of aortic and large-artery, small-vessel disease or other alterations in small arteries supplying the subcortical and basal ganglia white matter leading from the base of the brain, cerebral blood flow, blood-brain barrier disruption, a number of white matter lesions detected, a number of Lewy bodies detected, cerebral atrophy, hippocampal volume reduction, and cerebral spinal fluid levels offs-amyloid peptides or tau protein following a renal neuromodulation procedure as determined by qualitative or quantitative analysis (e.g., CT scan, PWV analysis, angiography, MRI, PET scan, etc.) before and after (e.g., 1, 3, 6, or 12 months after; 2, 3, 4, 5 or 10 years after) the renal neuromodulation procedure.

As discussed previously, the progression of vascular cognitive impairment may be related to chronic sympathetic overactivity (e.g., during middle age) and, correspondingly, the degree of sympathoexcitation in a patient may be related to the severity of the clinical presentation of vascular cognitive impairment in later life. The kidneys are positioned to be both a cause (via afferent nerve fibers) and a target (via efferent sympathetic nerves) of elevated central sympathetic drive. In some embodiments, renal neuromodulation can be used to reduce central sympathetic drive in a patient demonstrating one or more risk factors for vascular dysfunction in a manner that treats the patient for vascular changes in midlife and/or to prevent an incidence of vascular cognitive impairment in the patient in later life. In some embodiments, for example, MSNA can be reduced by at least about 10% in the patient within about three months after at least partially inhibiting sympathetic neural activity in nerves proximate a renal artery of the kidney. Similarly, in some instances whole body norepinephrine spillover to plasma can be reduced at least about 20%, about 30%, about 40%, about 45%, about 50% or a greater amount in the patient within about three months to about 12 months after at least partially inhibiting sympathetic neural activity in nerves proximate a renal artery of the kidney. Additionally, measured norepinephrine content (e.g., assessed via renal biopsy, assessed in real-time via intravascular blood collection techniques, etc.) can be reduced (e.g., at least about 5%, 10%, or by at least 20%) in the patient within about three months after at least partially inhibiting sympathetic neural activity in nerves proximate a renal artery innervating the kidney.

In one prophetic example, a patient having one or more suspected risk factors for the development of dementia can be subjected to a baseline assessment indicating a first set of measurable parameters corresponding to the one or more risk factors. Such parameters can include, for example, levels of central sympathetic drive (e.g., MSNA, whole body norepinephrine spillover), measured norepinephrine content (e.g., assessed via tissue biopsy), blood pressure, 24-hour blood pressure variability, inflammatory biomarker levels (e.g., IL-6, CRP), cholesterol levels, blood glucose levels, fasting blood insulin levels, measures of insulin sensitivity, body mass index, perceived cognitive functioning level (e.g., self-reporting, third-party reporting, etc.), one or more brain function test scores, and brain/body imaging for vascular remodeling (e.g., arteriole stiffness, arterial blood flow) and/or brain structural alterations (e.g., Lewy bodies, plaques, atrophy, atherosclerosis, blood brain barrier disruption, etc.). Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment; 2, 3, 4, 5 or 10 years following the treatment), the patient can be subjected to a follow-up assessment. The follow-up assessment can indicate a measurable improvement in one or more physiological parameters corresponding to the one or more suspected risk factors for the development of dementia and/or other cognitive impairment (e.g., mild cognitive impairment).

The methods described herein address the sympathetic excess that is thought to be an underlying factor in dementia progression or a central mechanism through which multiple dementia risk factors are manifest in patients. Currently, there are no therapies prescribed to address the effects of sympathetic excess in patients suspected of having a risk of developing dementia. Certain proposed therapies, such as lifestyle alterations (e.g., exercise, diet, etc.), blood pressure maintenance (e.g., administration of anti-hypertensive therapies), and reduction and/or maintenance of cholesterol may have significant limitations including limited efficacy and undesirable side effects, and may be subject to adverse or undesirable drug interactions when used in combination. Moreover, use of any drug regimens (e.g., anti-hypertensive, cholesterol-lowering, anti-inflammatory, etc.) have many challenges, including drug contraindications and drug adherence (particularly prior to onset of symptoms). For example, many of these drug regimens may require the patient to remain compliant with the treatment regimen starting in midlife and continue compliance over time. In contrast, neuromodulation can be a one-time or otherwise limited treatment that would be expected to have durable benefits to inhibit the long-term potential of developing dementia and thereby achieve a favorable patient outcome.

In some embodiments, patients demonstrating one or more risk factors associated with the development of dementia and/or having one or more physiological indicators of cognitive decline can be treated with renal neuromodulation alone. However, in other embodiments, combinations of therapies can be tailored based on specific conditions and dementia risk factors in a particular patient. For example, certain patients can be treated with combinations of therapies such as one or more conventional therapies for reducing blood pressure (e.g., anti-hypertensive drug(s)) and treated with one or more neuromodulation treatments. In another example, renal neuromodulation can be combined with cholesterol lowering agents (e.g., statins), anti-inflammatory therapy (e.g., drug(s)), as well as weight loss and lifestyle change recommendations/programs.

Treatment of dementia risk factors, mild cognitive impairment, or symptoms and conditions associated with dementia may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

IV. SELECTED EXAMPLES OF NEUROMODULATION MODALITIES

As noted previously, complete or partial neuromodulation of a target renal sympathetic nerve in accordance with embodiments of the present technology can be electrically-induced, thermally-induced, chemically-induced, or induced in another suitable manner or combination of manners at one or more suitable locations along one or more renal blood vessels during a treatment procedure. For example, neuromodulation may be achieved using various modalities, including for example monopolar or bipolar RF energy, pulsed RF energy, microwave energy, laser light or optical energy, magnetic energy, ultrasound energy (e.g., intravascularly delivered ultrasound, extracorporeal ultrasound, high-intensity focused ultrasound (HIFU)), direct heat energy, radiation (e.g., infrared, visible, gamma) or cryotherapeutic energy, chemicals (e.g., drugs or other agents), or combinations thereof. Where a system uses a monopolar configuration, a return electrode or ground patch fixed externally on the subject can be used. In certain embodiments, neuromodulation may utilize one or more devices including, for example, catheter devices such as the Symplicity Spyral™ catheter (Medtronic, Inc.). Other suitable thermal devices are described in U.S. Pat. Nos. 7,653,438, 8,347,891, and U.S. patent application Ser. No. 13/279,205, filed Oct. 21, 2011. Other suitable devices and technologies are described in U.S. patent application Ser. No. 13/279,330, filed Oct. 23, 2011, International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. Other examples of suitable direct heat devices are described in International Patent Application No. PCT/US2014/023738 filed Mar. 11, 2014, and U.S. patent application Ser. No. 14/203,933, filed Mar. 11, 2014. All of the foregoing patent references are incorporated herein by reference in their entireties.

In those embodiments of the methods disclosed herein that utilize partial ablation, the level of energy delivered to the target artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities. In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial neuromodulation of a renal sympathetic nerve can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic nerve can slow or potentially block conduction of neural signals to produce a prolonged or permanent reduction in sympathetic activity. A variety of suitable types of energy, such as those mentioned above, can be used to stimulate and/or heat tissue at a treatment location. In some embodiments, neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective neuromodulation of a target sympathetic nerve. For example, cryotherapeutic treatment can include cooling tissue at a treatment location in a manner that modulates neural function. For example, sufficiently cooling at least a portion of a target sympathetic nerve can slow or potentially block conduction of neural signals to produce a prolonged or permanent reduction in sympathetic activity associated with the target sympathetic nerve. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion.

Neuromodulation using a cryotherapeutic treatment in accordance with embodiments of the present technology can include cooling a structure proximate an inner surface of a vessel or chamber wall such that tissue is effectively cooled to a depth where sympathetic nerves reside. For example, a cooling assembly of a cryotherapeutic device can be cooled to the extent that it causes therapeutically-effective, cryogenic neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause organs and tissues to rise and fall and thereby move the arteries and other structures associated with these organs and tissues. In addition, blood flow is pulsatile and can cause structures associated with the kidneys to pulse. Cryogenic adhesion also can facilitate intravascular or intraluminal positioning, particularly in relatively-small structures (e.g., renal branch arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In certain embodiments, monitoring, assessing and/or determining neuromodulation efficacy can be accomplished by detecting changes in the level of one or more surrogate biomarkers (e.g., a biomarker that directly or indirectly correlates with sympathetic nerve activity in the patient, a biomarker that directly or indirectly correlates with hypertension, arterial stiffness and/or an inflammatory response in the patient) in serum, plasma and/or urine in response to neuromodulation. Systems and method for monitoring the efficacy of neuromodulation by measuring the levels of one or more biomarkers associated with neuromodulation including, for example, proteins or non-protein molecules that exhibit an increase or decrease in level or activity in response to neuromodulation are described in, e.g., International Patent Application No. PCT/US2013/030041, filed Mar. 8, 2013, and International Patent Application No. PCT/US2015/047568, filed Aug. 28, 2015, the disclosures of which are incorporated herein by reference in their entireties. In other embodiments, measured levels of protein or non-protein molecules (e.g., associated with norepinephrine spillover, associated with inflammatory responses, etc.) that exhibit an increase or decrease in level or activity in response to targeted neuromodulation can be assessed pre- and post-neuromodulation in tissue biopsies.

III. SELECTED EMBODIMENTS OF RENAL NEUROMODULATION SYSTEMS AND DEVICES

Figure 3:
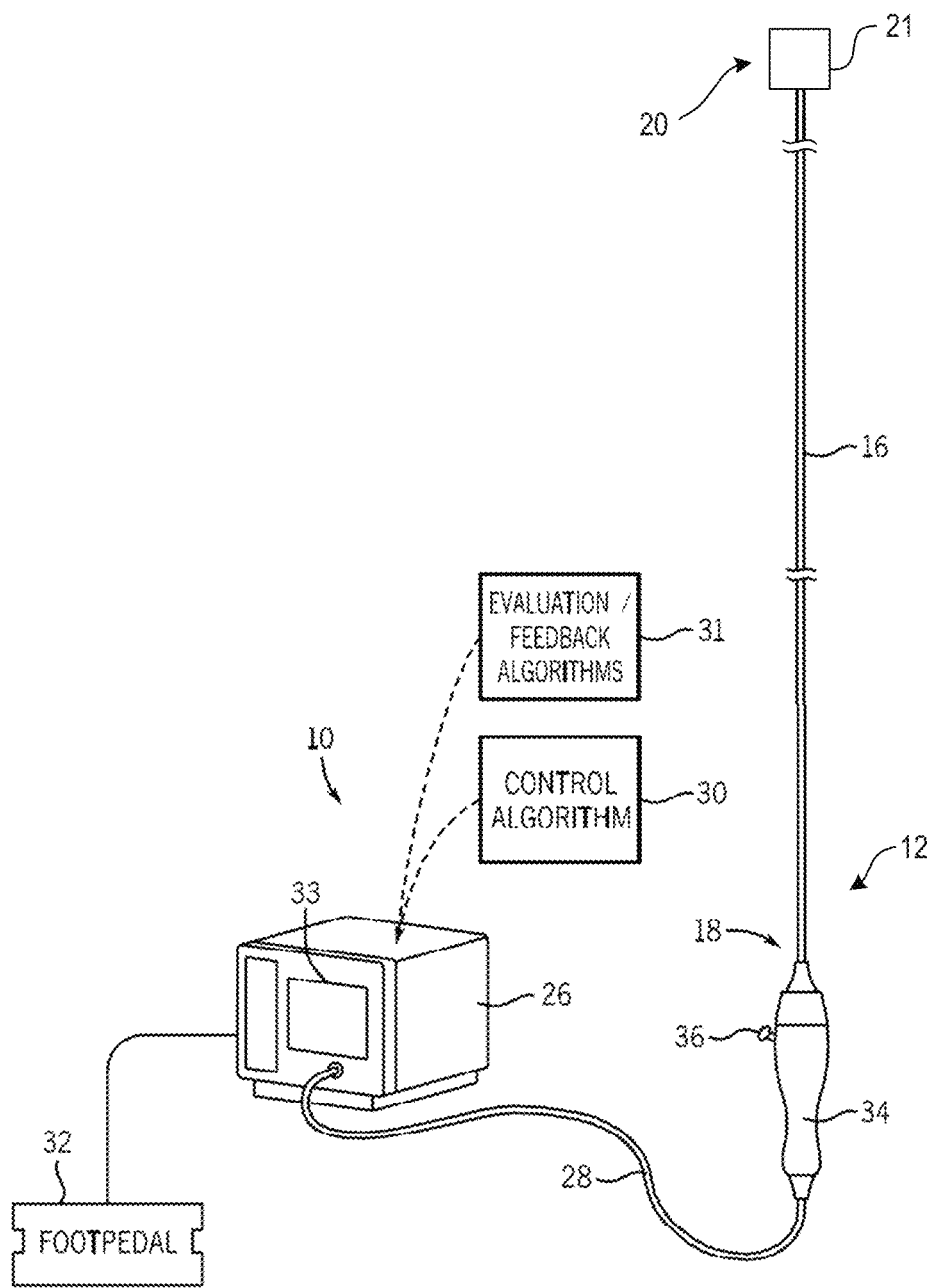
FIG. 3 illustrates an intravascular neuromodulation system configured in accordance with an embodiment of the present technology.

FIG. 3 illustrates a renal neuromodulation system 10 configured in accordance with an embodiment of the present technology. The system 10, for example, may be used to perform therapeutically-effective renal neuromodulation on a patient (a) to reduce the risk of occurrence of vascular cognitive impairment (e.g., vascular dementia) and/or other forms of dementia (e.g., Alzheimer's disease), (b) to reduce a calculated dementia risk score (e.g., a probability of developing dementia in later life), (c) to reduce a severity of neurological symptoms relating to dementia, and/or (d) to slow a rate of progression of neurological symptoms relating to dementia. In one embodiment, the patient may be diagnosed with increased overall sympathetic activity, and, in particular, conditions associated with central sympathetic overstimulation and increased risk of developing dementia in later life, such as hypertension, blood pressure variability, systemic inflammation, arterial stiffness, metabolic syndrome, insulin resistance and diabetes, among others.

The system 10 includes an intravascular treatment device 12 operably coupled to an energy source or console 26 (e.g., a RF energy generator, a cryotherapy console). In the embodiment shown in FIG. 3, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can be configured to ablate nerve tissue and/or for monitoring one or more physiological parameters within the vasculature. Accordingly, a neuromodulation assembly 21 suitable for ablation may include one or more electrodes, transducers, energy-delivery elements or cryotherapeutic cooling assemblies. Neuromodulation assemblies 21 suitable for monitoring may also include a nerve monitoring device and/or blood collection/analysis device. In some embodiments, the neuromodulation assembly 21 can be configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In further embodiments, the neuromodulation assembly 21 can include one or more electrodes configured to deliver ablation energy and/or stimulation energy. In some arrangements, the neuromodulation assembly 21 can include one or more sensor(s) for detecting impedance or nerve monitoring signals. In any of the foregoing embodiments, the neuromodulation assembly 21 may comprise an irrigated electrode.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The console 26 can be configured to deliver the treatment energy via an automated control algorithm 30 and/or under the control of the clinician. In addition, the console 26 may include one or more evaluation and/or feedback algorithms 31 to provide feedback to the clinician before, during, and/or after therapy.

The console 26 can further include a device or monitor that may include processing circuitry, such as a microprocessor, and a display 33. The processing circuitry may be configured to execute stored instructions relating to the control algorithm 30. The console 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or balloon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

IV. SELECTED EXAMPLES OF TREATMENT PROCEDURES FOR RENAL NEUROMODULATION

A. Achieving Intravascular Access to the Renal Artery

Figure 4A:
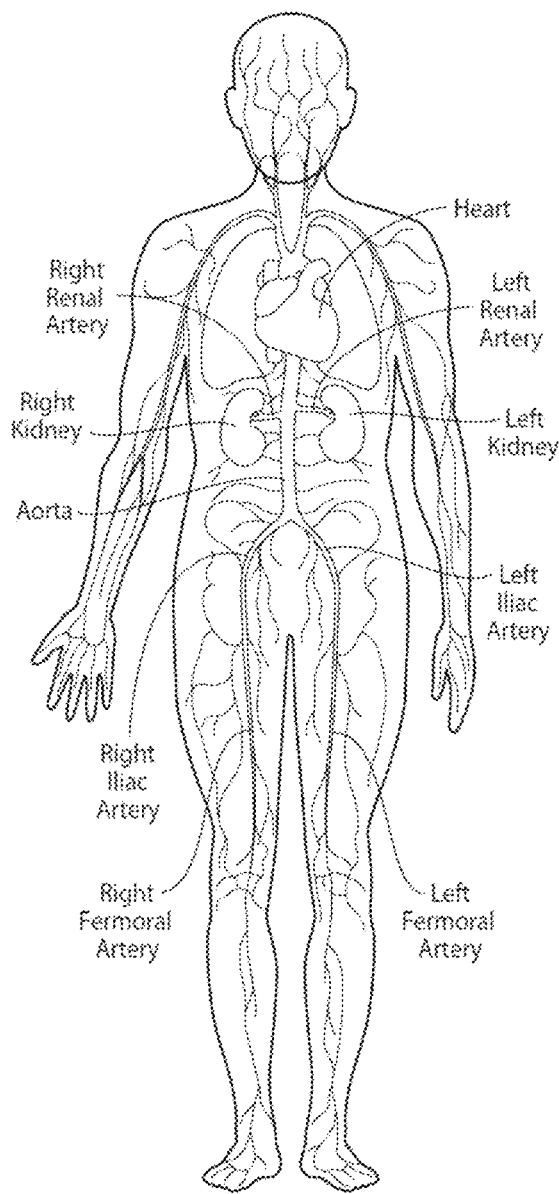
FIGS. 4A and 4B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 4B:
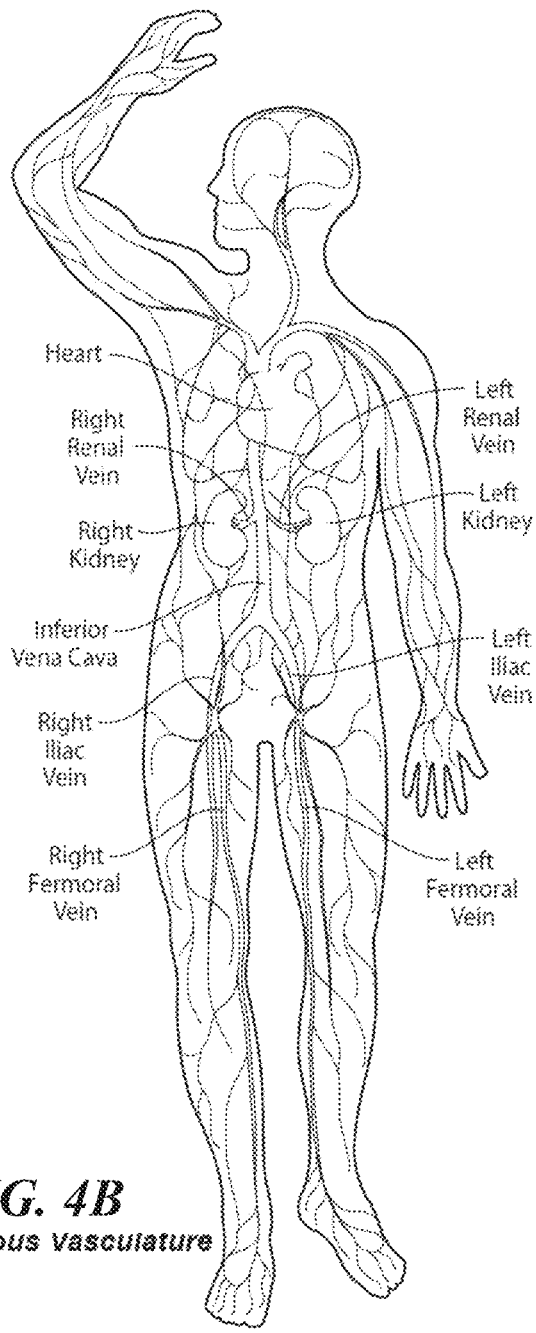

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

B. Properties and Characteristics of the Renal Vasculature

Properties and characteristics of the renal vasculature impose challenges to both access and treatment methods, and to system/device designs. Since neuromodulation of a left and/or right renal plexus RP may be achieved in accordance with embodiments of the present technology through intravascular access, various aspects of the design of apparatus, systems, and methods for achieving such renal neuromodulation are disclosed herein. Aspects of the technology disclosed herein address additional challenges associated with variation of physiological conditions and architecture across the patient population and/or within a specific patient across time, as well as in response to disease states, such as hypertension, atherosclerosis, vascular disease, chronic inflammatory condition, insulin resistance, diabetes, metabolic syndrome, etc. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery. For example, spiral or helical CT technology can be used to produce 3D images of the vascular features for individual patients, and intravascular path choice as well as device size/diameter, length, flexibility, etc. can be selected based upon the patient's specific vascular features.

In addition to complicating renal arterial access, specifics of the renal anatomy also complicate establishment of stable contact between neuromodulatory apparatus and a luminal surface or wall of a renal blood vessel. When the neuromodulatory apparatus includes an energy delivery element, such as an electrode, transducer, or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse). To address these challenges, the treatment device or applicator may be designed with relative sizing and flexibility considerations. For example, the renal artery may have an internal diameter in a range of about 2-10 mm and the treatment device can be delivered using a 3, 4, 5, 6, 7 French, or in some cases, a 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a renal artery and facilitating stable contact between neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant (e.g., 1-3 mm) from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery. Accordingly, sensory feedback, such as impedance and temperature, can be used to assess whether a desired energy distribution is administered at the treatment site and can, in some instances, be used to change an energy delivery algorithm in real-time to adjust for varying fluctuations in the properties and conditions affecting heat transfer dynamics at the treatment site.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of creating a circumferential lesion or ablation may outweigh the potential of renal artery stenosis or the risk may be mitigated with certain embodiments or in certain patients and creating a circumferential lesion or ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

C. Neuromodulation of Renal Sympathetic Nerve at Treatment Site

Figure 5:
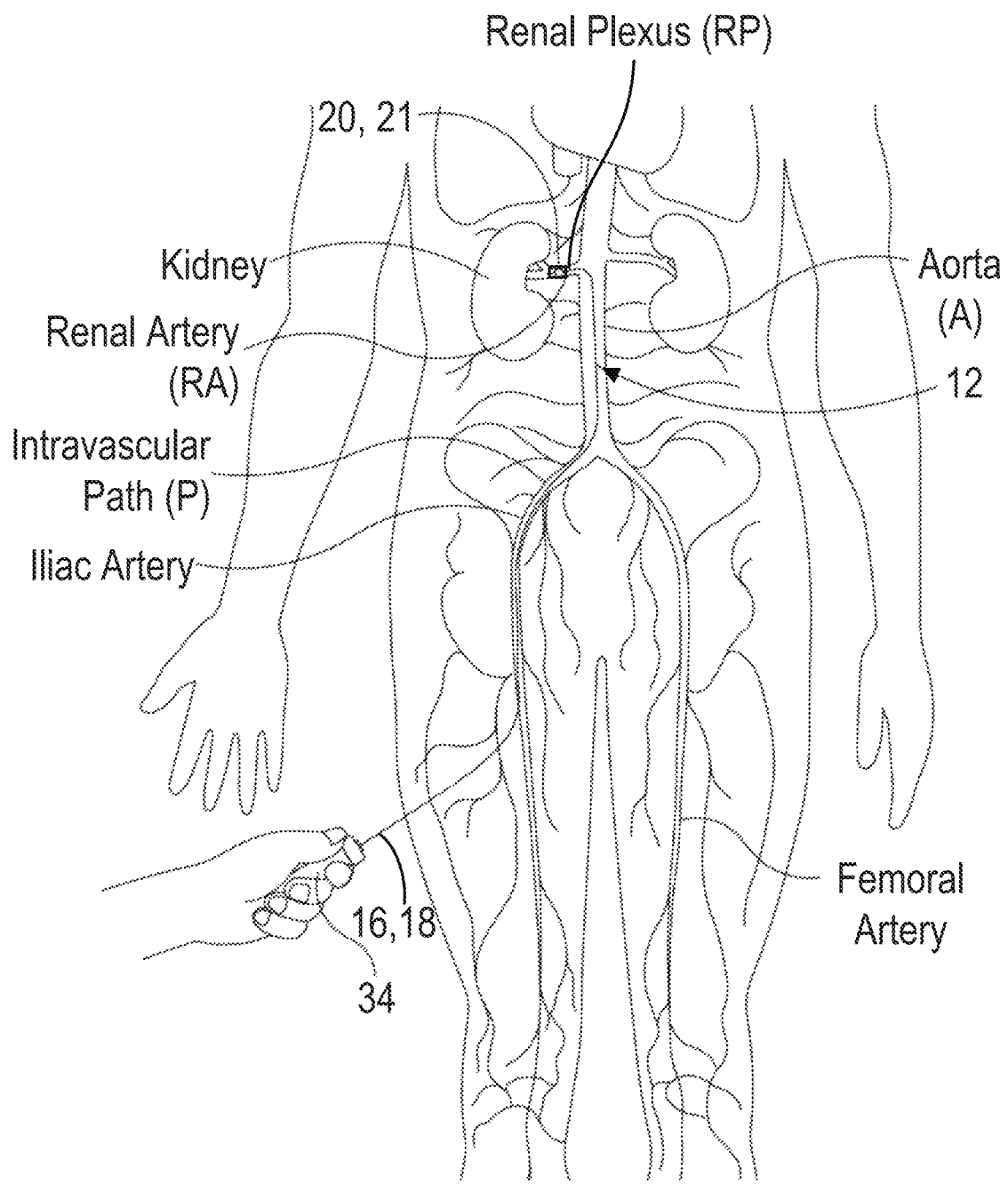
FIG. 5 illustrates modulating renal nerves with a neuromodulation system configured in accordance with an embodiment of the present technology.

FIG. 5 illustrates modulating renal nerves with an embodiment of the system 10 (FIG. 3). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP.

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured form a partially-circumferential lesion or a fully-circumferential lesion at a single longitudinal segment or zone of the vessel. During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

Furthermore, a treatment procedure can include treatment at any suitable number of treatment locations, e.g., a single treatment location, two treatment locations, or more than two treatment locations. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16 fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

Figure 6:
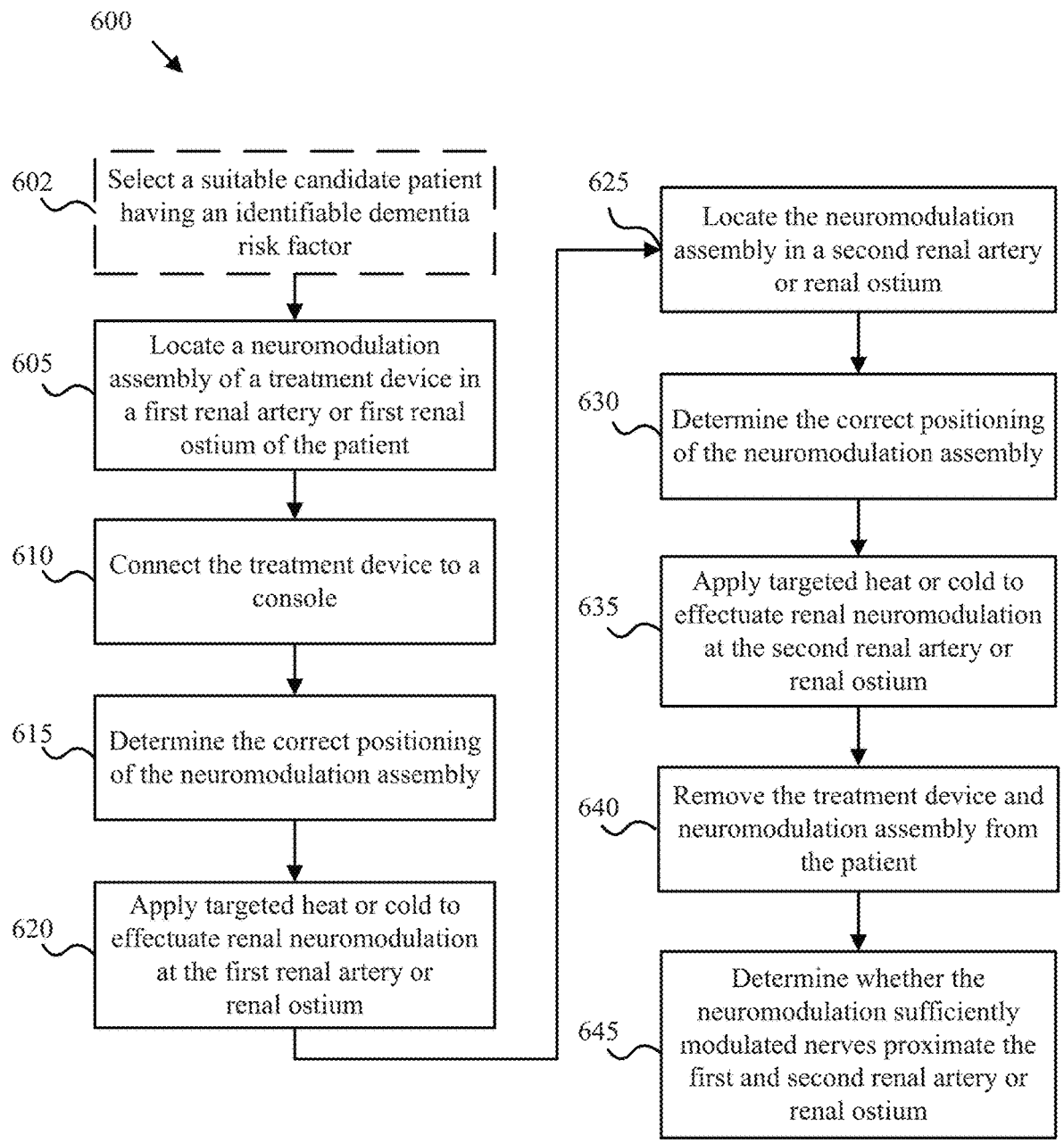
FIG. 6 is a block diagram illustrating a method of modulating renal nerves in accordance with an embodiment of the present technology.

FIG. 6 is a block diagram illustrating a method 600 of modulating renal nerves using the system 10 described above with reference to FIGS. 3 and 5. With reference to FIGS. 3, 5 and 6 together, the method 600 can optionally include selecting a suitable candidate patient having an identifiable dementia risk factor for performing renal neuromodulation (block 602). For example, a suitable patient can include a patient having a predictive dementia risk score above a threshold level, a patient having one or more measurable risk factors for developing dementia, a patient having one or more identifiable markers of cognitive decline, a patient diagnosed with mild cognitive impairment, a midlife aged patient having a family history of developing dementia and/or a patient diagnosed with early stage dementia.

Targeting SNS nerves innervating the kidneys is expected to result in reduced or lower both renal and central SNS nerve activity, thereby inhibiting, preventing, slowing, disrupting or reversing physiological pathways associated with cognitive decline and/or lower a risk associated with developing dementia in the patient. In particular, targeting the renal nerve for neuromodulation is anticipated to reduce renal norepinephrine spillover, whole body norepinephrine spillover, and reduce central sympathetic drive (e.g., reduce a level of efferent SNS nerve firing) in the patient, thereby inhibiting, preventing, slowing, disrupting or reversing conditions proposed to increase a patient's risk of developing dementia. Without being bound by theory, renal neuromodulation is anticipated to address several potential underlying contributing causes of dementia, for example, high blood pressure, arterial stiffness, vascular inflammation, systemic inflammation, metabolic disorders, obesity and insulin resistance, among others.

The method 600 can include intravascularly locating the neuromodulation assembly 21 in a delivery state (e.g., low-profile configuration) to a first target site in or near a first renal blood vessel (e.g., first renal artery) or first renal ostium (block 605). The treatment device 12 and/or portions thereof (e.g., the neuromodulation assembly 21) can be inserted into a guide catheter or sheath to facilitate intravascular delivery of the neuromodulation assembly 21. In certain embodiments, for example, the treatment device 12 can be configured to fit within an 8 Fr guide catheter or smaller (e.g., 7 Fr, 6 Fr, etc.) to access small peripheral vessels. A guide wire (not shown) can be used to manipulate and enhance control of the shaft 16 and the neuromodulation assembly 21 (e.g., in an over-the-wire or a rapid-exchange configuration). In some embodiments, radiopaque markers and/or markings on the treatment device 12 and/or the guide wire can facilitate placement of the neuromodulation assembly 21 at the first target site (e.g., a first renal artery or first renal ostium of the patient). In some embodiments, a contrast material can be delivered distally beyond the neuromodulation assembly 21, and fluoroscopy and/or other suitable imaging techniques can be used to aid in placement of the neuromodulation assembly 21 at the first target site.

The method 600 can further include connecting the treatment device 12 to the console 26 (block 610), and determining whether the neuromodulation assembly 21 is in the correct position at the target site and/or whether the neuromodulation assembly (e.g., electrodes or cryotherapy balloon) is functioning properly (block 615). Once the neuromodulation assembly 21 is properly located at the first target site and no malfunctions are detected, the console 26 can be manipulated to initiate application of an energy field to the target site to cause electrically-induced and/or thermally-induced partial or full denervation of the kidney (e.g., using electrodes or cryotherapeutic devices). Accordingly, heating and/or cooling of the neuromodulation assembly 21 causes modulation of renal nerves at the first target site to cause partial or full denervation of the kidney associated with the first target site (block 620).

In one example, the treatment device 12 can be an RF energy emitting device and RF energy can be delivered through energy delivery elements or electrodes to one or more locations along the inner wall of the first renal blood vessel or first renal ostium for predetermined periods of time (e.g., 120 seconds). In some embodiments, multiple treatments (e.g., 4-6) may be administered in both the left and right renal blood vessels (e.g., renal arteries) to achieve a desired coverage and/or desired inhibition of sympathetic neural activity in the body.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

A technical objective of a treatment may be, for example, to heat tissue to a desired depth (e.g., at least about 3 mm) to a temperature that would lesion a nerve (e.g., about 65° C.). A clinical objective of the procedure typically is to neuromodulate (e.g., lesion) a sufficient number of renal nerves (either efferent or afferent nerves) to cause a reduction in sympathetic tone or drive to the kidneys. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.)

In a specific example of using RF energy for renal nerve modulation, a clinician can commence treatment which causes the control algorithm 30 (FIG. 3) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In another specific example, the treatment device 12 can be a cryogenic device and cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the neuromodulation assembly 21). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 21 can optionally then be located at a second target site in or near a second renal blood vessel (e.g., second renal artery) or second renal ostium (block 625), and correct positioning of the assembly 21 can be determined (block 630). In selected embodiments, a contrast material can be delivered distally beyond the neuromodulation assembly 21 and fluoroscopy and/or other suitable imaging techniques can be used to locate the second renal artery. The method 600 continues by applying targeted heat or cold to effectuate renal neuromodulation at the second target site to cause partial or full denervation of the kidney associated with the second target site (block 635).

After providing the therapeutically-effective neuromodulation energy (e.g., cryogenic cooling, RF energy, ultrasound energy, etc.), the method 600 may also include removing the treatment device 12 (e.g., catheter) and the neuromodulation assembly 21 from the patient (block 640). In some embodiments, the neuromodulation assembly 21 can be an implantable device and a treatment procedure can include implanting the neuromodulation assembly 21 at a suitable treatment location within the patient. Other treatment procedures for modulation of target sympathetic nerves in accordance with embodiments of the present technology are also possible.

The method 600 may also include determining whether the neuromodulation sufficiently modulated nerves or other neural structures proximate the first and second target sites (block 645). For example, the process of determining whether the neuromodulation therapeutically treated the nerves can include determining whether nerves were sufficiently modulated or otherwise disrupted to reduce, suppress, inhibit, block or otherwise affect the afferent and/or efferent renal signals (e.g., by evaluation of suitable biomarkers, stimulation and recording of nerve signals, etc.). Examples of suitable biomarkers and their detection are described in International Patent Application No. PCT/US2013/030041, filed Mar. 8, 2013, and International Patent Application No. PCT/US2015/047568, filed Aug. 28, 2015, the disclosures of which are incorporated herein by reference in their entireties. Other suitable devices and technologies, such as endovascular intraoperative renal nerve monitoring devices are described in International Patent Application No. PCT/US12/63759, filed Jan. 29, 2013, and incorporated herein by reference in its entirety.

In a further embodiment, patient assessment could include determining whether the neuromodulation therapeutically treated the patient for one or more conditions associated with underlying contributing causes of dementia, e.g., high blood pressure, arterial stiffness, vascular inflammation, systemic inflammation, metabolic disorders, obesity and insulin resistance, among others. Assessment of certain suitable biomarkers and/or nerve signals may be made immediately or shortly after neuromodulation (e.g., about 15 minutes, about 24 hours, or about 7 days post-neuromodulation). In further embodiments, patient assessment could be performed at time intervals (e.g., about 1 month, 3 months, 6 months, 12 months) following neuromodulation treatment. For example, the patient can be assessed for measurements of blood pressure, blood pressure variability, sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, measures of sympathetic activity (e.g., MSNA, renal and/or total body norepinephrine spillover, plasma norepinephrine levels, and heart rate variability), peripheral inflammatory markers (e.g., IL-6, CRP, etc.), and markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio).

In other embodiments, various steps in the method 600 can be modified, omitted, and/or additional steps may be added. In further embodiments, the method 600 can have a delay between applying therapeutically-effective neuromodulation energy to a first target site at or near a first renal artery or first renal ostium and applying therapeutically-effective neuromodulation energy to a second target site at or near a second renal artery or second renal ostium. For example, neuromodulation of the first renal artery can take place at a first treatment session, and neuromodulation of the second renal artery can take place a second treatment session at a later time.

Figure 7:
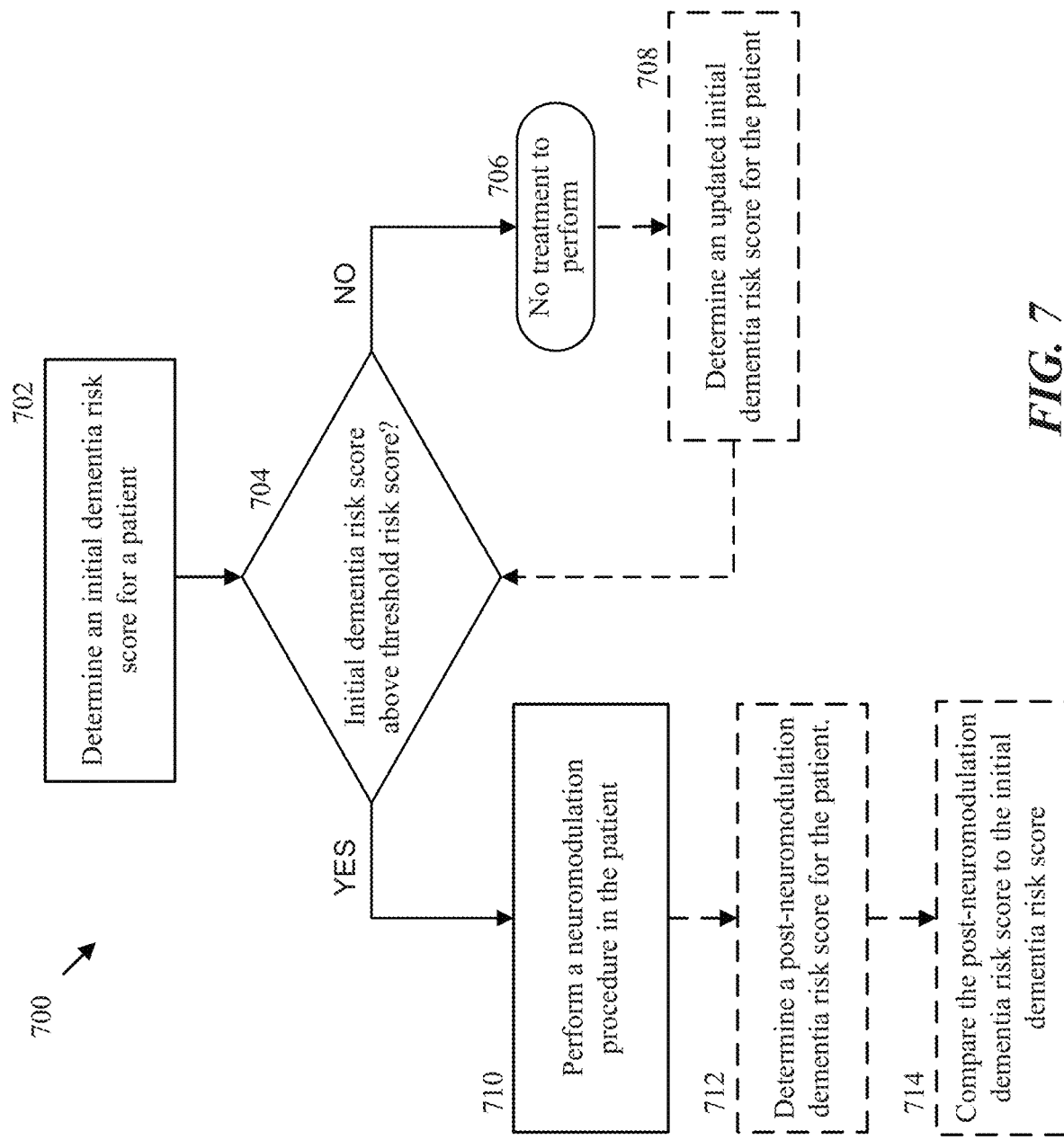
FIG. 7 is a block diagram illustrating a method for improving a dementia risk score for a patient in accordance with an embodiment of the present technology.

FIG. 7 is a block diagram illustrating a method 700 for improving a dementia risk score for a patient in accordance with aspects of the present technology. In a first step, the method 700 can include determining an initial dementia risk score for a patient (block 702). For example, one or more suitable dementia risk score calculating techniques or tools can be used to establish a dementia risk score or a probability of developing dementia in later life (e.g., within 10 years, within 20 years, etc.) as described above (Kivipelto, M., et al. *Lancet Neurol,* 2006, 5: 735-741). In decision block 704, the initial dementia risk score can be evaluated against a threshold risk score or value. If the initial dementia risk score is not above the threshold risk score, there is no need to reduce the dementia risk score for the patient at the current time and no treatment is selected to perform (block 706). In such a patient, a clinician may recommend monitoring the patient's dementia risk score over time. For example, a clinician can optionally determine an updated initial dementia risk score for the patient after a determined time lapse (e.g., within in 1 year, within 2 years, within 5 years, within 10 years, etc.) (block 708). Following each dementia risk score evaluation (block 708), the patient dementia risk score is evaluated against the threshold risk score or value (decision block 704).

If the patient dementia risk score from method step 702, or from the optional method step 708, is higher than the threshold risk score, the method 700 can include performing a neuromodulation procedure in the patient (block 710). In one example, the patient can be a suitable candidate patient as identified in method step 602 of method 600 described above, and the neuromodulation procedure can be as described in continuing steps of method 600. In other embodiments, a clinician can perform an alternative neuromodulation procedure at method step 710. For example, neuromodulation of other target (e.g., non-renal) sympathetic nerves or neuromodulation in a single renal blood vessel (e.g., renal artery) may be performed on the patient.

The method 700 is expected to improve the patient's dementia risk score or reduce a probability of developing dementia in later life. Optionally, the clinician can further determine a post-neuromodulation dementia risk score for the patient (block 712). For example, the patient can be evaluated using the dementia risk score calculator to assess the patient's post-neuromodulation risk of developing dementia in later life (e.g., within 10 years, within 20 years, etc.). If the post-neuromodulation dementia risk score is determined for the patient in step 712, the method includes comparing the post-neuromodulation dementia risk score to the initial dementia risk score (block 714). In determining if the method 700 is successful, the post-neuromodulation dementia risk score is lower than the patient's initial dementia risk score as determined in step 702 (or updated dementia initial risk score as determined in step 708). In some examples, the post-neuromodulation dementia risk score is lower than the initial dementia risk score by about 5%, about 10%, about 20% or about 30%. In other embodiments, the post-neuromodulation dementia risk score is lower than the initial dementia risk score by more than 30%. In certain embodiments, the post-neuromodulation dementia risk score can be lower than the threshold risk score.

VII. EXPERIMENTAL EXAMPLES

Example 1

This section describes an example of the outcome of renal neuromodulation on human patients. A total of 45 patients (mean age of 58±9 years) diagnosed with essential hypertension were treated with percutaneous, catheter based renal nerve ablation. Treatment included RF energy delivery to the renal artery using a single-electrode Symplicity Flex™ catheter commercially available from Medtronic, Inc., of 710 Medtronic Parkway, Minneapolis, Minn. 55432-5604. In this human trial, a radiotracer dilution method was used to assess overflow of norepinephrine from the kidneys into circulation before and 15-30 days after the procedure in 10 patients. Bilateral renal-nerve ablation resulted in a marked reduction in mean norepinephrine spillover from both kidneys: 47% (95% confidence interval) one month after treatment.

In a similar human trial where bilateral renal nerve ablation was performed in 70 patients, whole-body norepinephrine levels (i.e., a measure of "total" sympathetic activity), fell by nearly 50% after renal nerve ablation and measurement of muscle sympathetic nerve activity showed a drop of 66% over 6 months, further supporting the conclusion that total sympathetic dive was reduced by the renal denervation procedure in this patient group.

Example 2

Example 2 describes the outcome of catheter-based renal neuromodulation on human patients diagnosed with hypertension. Patients selected having a baseline systolic blood pressure of 160 mm Hg or more (≥150 mm Hg for patients with type 2 diabetes) and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, $p<0.0001$), whereas they did not differ from baseline in the control group (change of 1/0 mm Hg, baseline of 178/97 mm Hg, $p=0.77$ systolic and $p=0.83$ diastolic). Between-group differences in blood pressure at 6 months were 33/11 mm Hg ($p<0.0001$). At 6 months, 41 (84%) of 49 patients who underwent renal neuromodulation had a reduction in systolic blood pressure of 10 mm Hg or more, compared with 18 (35%) of 51 control patients ($p<0.0001$).

Example 3

Example 3 describes the outcome of catheter-based renal neuromodulation on animal subjects in an additional experiment. In this example (and referring to FIGS. 8A and 8B), studies using the pig model were performed using a multi-electrode Symplicity Spyral™ catheter or a single-electrode Symplicity Flex™ catheter along with a Symplicity G3™ generator. The catheters and generator are commercially available from Medtronic, Inc. The catheters were used in these cohorts of animals (n=66) to create multiple RF ablations in the renal vasculature. Cortical axon density in the renal cortex (FIG. 8A) and renal cortical norepinephrine (NE) concentration (FIG. 8B) were used as markers to measure procedural efficacy.

As shown in FIG. 8A, cortical axon area (per $mm^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

Figure 8B:
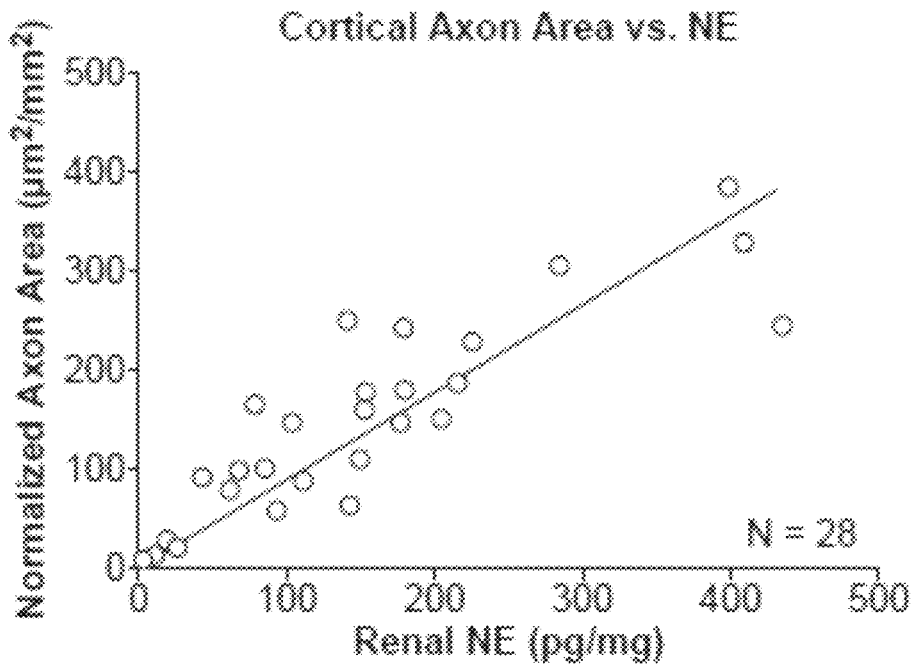
FIG. 8B is a series of graphs illustrating the response correlation between normalized cortical axon area vs. norepinephrine concentration and norepinephrine concentration vs. extent of nerve ablation along the artery of the animal subjects of FIG. 8A.
Figure 8B:
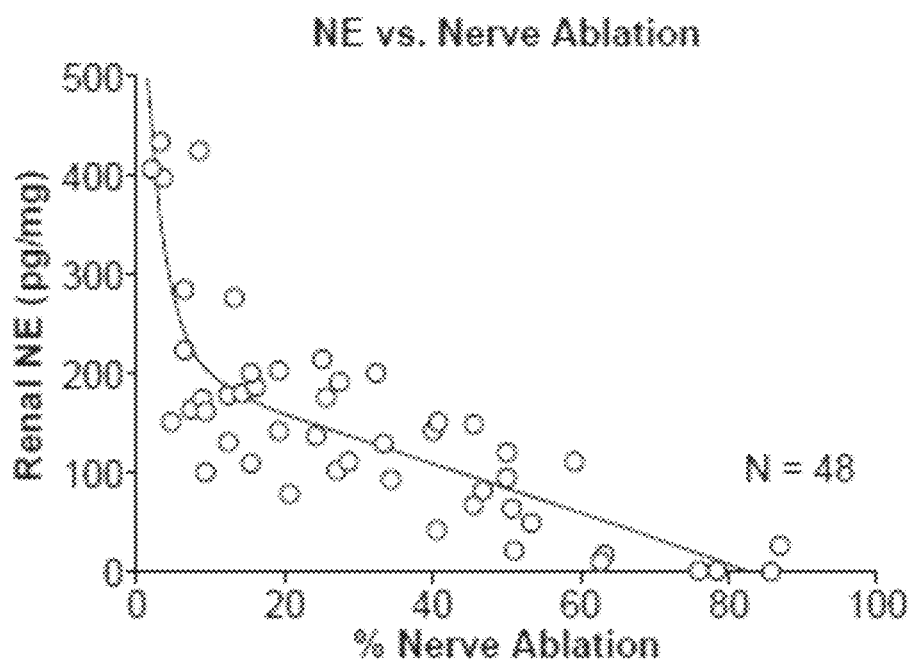

FIG. 8B includes (a) a graph of normalized cortical axon area vs. renal NE concentration, and (b) a graph of renal NE concentration vs. extent (%) of nerve ablation. Referring to the table of FIG. 8A and the two graphs of FIG. 8B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level compared with the pigs in the control group. This is further shown by the first graph of FIG. 8B, which demonstrates that a decrease in cortical axon area correlates with a decrease in NE levels. Referring to the second graph of FIG. 8B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability, and further suggest that neuromodulation of SNS fibers innervating a target tissue and/or organ (such as the kidney) result in a significant decrease in local NE concentration.

Example 4

Example 4 describes an example of the outcome of renal neuromodulation on human patients. Markers of cardiovascular inflammation and remodeling were assessed (Dörr, O., et al., *Clin Res Cardiol*, 2015, 104: 175-184). A total of 60 patients (mean age of 67.9±9.6 years) diagnosed with resistant arterial hypertension were treated with percutaneous, catheter-based renal sympathetic denervation. Treatment included RF energy delivery to the renal artery using a Symplicity™ catheter system commercially available from Medtronic, Inc. In this human trial, a therapeutic response was defined as a systolic blood pressure (BP) reduction of >10 mmHg in the office blood pressure measurement 6 months after renal denervation. Of the 60 patients, 49 patients (82%) were classified as responders with a mean systolic BP reduction of >10 mmHg. Venous blood samples for determination of biomarkers of inflammation (e.g., IL-6, high-sensitive C-reactive protein (hsCRP)) and markers of vascular remodeling (matrix metalloproteinases (MMP-2 and MMP-9), tissue inhibitors of matrix metalloproteinases (TIMP-1)) were collected at baseline (prior to renal denervation) and 6 months after renal denervation for all patients.

Collected data from all patients demonstrated that bilateral renal nerve denervation resulted in a significant reduction in mean office systolic BP of 26.4 mmHg (169.3±11.3 mmHg at baseline vs. 142.9±13.8 mmHg at follow-up; $p<0.001$). The procedure further resulted in a significant reduction in the serum levels of hsCRP (3.6 mg/dL at baseline vs. 1.7 mg/dL at follow-up, $p<0.001$), and a significant reduction in the pro-inflammatory cytokine IL-6 (4.04 pg/mL at baseline vs. 2.2 pg/mL at follow-up, $p<0.001$) six months after treatment. Additionally, the procedure resulted in a significant increase in the serum levels of MMP-9 (425.2 ng/mL at base line vs. 574.1 ng/mL at follow-up, $p=0.02$), and in serum levels of MMP-2 (192.3 ng/mL at baseline vs. 231.3 ng/mL at follow-up, $p<0.001$). There were no significant changes in TIMP-1 6 months after renal denervation. Notably, of non-responders (e.g., patients with a BP reduction of <10 mmHg), serum levels of hsCRP still decreased (3.2 mg/dL at baseline vs. 2.4 mg/dL at follow-up, $p=0.09$), and serum levels of IL-6 still decreased (3.1 pg/mL at baseline vs. 2.7 pg/mL at follow-up, $p=0.16$), although there was a significantly greater beneficial effect of renal denervation on biomarker levels in BP responders when compared with non-responders.

These findings suggest that catheter-based renal neuromodulation exhibits a positive vascular and systemic effect on mediators of inflammation, IL-6 and hsCRP, and inhibitors (MMP-9 and MMP-2) of deleterious cardiovascular remodeling. Low serum levels of MMP-9 and MMP-2 have been found to be essential to damaging vascular remodeling found in essential hypertension and progression of end-organ damage These findings suggest that levels of MMP-9 and MMP-2, which are involved in ECM turnover in different tissues, including the arterial wall, can be elevated post-renal neuromodulation, and, without being bound by theory, are postulated to be beneficial in reversal of damage to the vessels caused by inflammation, cardiovascular disease and/or hypertension. As elevated inflammatory biomarkers, such as IL-6 and CRP, have been proposed as predictors and possible contributors of incidence of dementia, these results demonstrate that renal neuromodulation may be useful to reduce a risk associated with the development of dementia in a patient (Koyama, A. et al., *J Gerontol A Biol Sci Med Sci.*, 2013, 68(4): 433-440; Metti, A. L. and Cauley, J. A., *Neurodegener Dis Manag.*, 2012, 2(6): 609-622). In addition to lowering systolic BP in (responsive) hypertensive patients, these findings suggest that renal denervation has a positive effect on biomarkers of inflammation (e.g., IL-6, hsCRP) and cardiovascular remodeling (e.g., MMP-2, MMP-9) separate from and in addition to the effect on blood pressure.

Example 5

Example 5 describes an example of the effects of renal neuromodulation on 24-hour blood pressure (BP) variability in human patients. Increased BP variability is associated with poorer cognitive function in older people and has been found to predict a greater decline in measures of global cognitive function over a 5-year follow-up (McDonald, C. et al., *J Hypertens.*, 2016, epub 34:000-000). In this example, a total of 11 patients (mean age of 68.9±7.0 years) diagnosed with resistant arterial hypertension (baseline systolic BP 189±23 mmHg) were treated with bilateral percutaneous, catheter-based renal sympathetic denervation (Zuern, C. S., et al., *Front. Physiol*, 2012, 3(134): 1-8). Treatment included RF energy delivery to the renal artery using a Symplicity™ system including a Symplicity Flex™ catheter. Up to six ablations at 8 watts for 2 minutes each were performed in both renal arteries. Treatments were delivered from the first distal main renal artery bifurcation to the ostium proximally and were spaced longitudinally and rotationally under fluoroscopic guidance. BP variability was measured by 24-hour systolic arterial BP before renal denervation and at 6 months after renal denervation.

In patients with resistant hypertension, renal denervation resulted in significant reduction of BP variability over 24 hours. In 10 of the 11 patients, standard deviation of 24 hour systolic arterial BP was reduced (16.9±4.6 at baseline vs. 13.5±2.5 mmHg at follow-up, p=0.003) 6 months post neuromodulation. These findings suggest that patients treated with renal neuromodulation will have decreased systolic BP variability and instability which will reduce the patient's likelihood (e.g., lower level of risk) of developing, progressing or worsening cognitive decline.

Example 6

Example 6 describes a method for treating human patients with renal neuromodulation and anticipated outcomes of such treatment. In this example, human patients having one or more risk factors for developing dementia will be treated with renal denervation and a method of treatment includes modulating nerve tissue surrounding the main renal artery (e.g., locations along the main renal vessel, locations at or near the bifurcation, etc.) and/or modulating nerve tissue surrounding one or more primary branch trunks (e.g., proximal portion of one or more primary branch vessels distal to the bifurcation).

For patients undergoing distal main renal artery treatment, modulating nerve tissue includes forming up to about six lesions at the distal segment of the renal artery and within a distance of approximately 6 mm proximal to the branch point within the renal artery using the Symplicity Flex™ catheter. The longitudinal spacing between the lesions may be approximately 2 mm, with a lesion footprint of approximately 2 mm each. For example, a first lesion can be formed about 5-6 mm from the bifurcation. The catheter can then be proximally retracted 1-2 mm and rotated 90 degrees followed by formation of a second lesion. Further lesions can be formed by sequential movement of the catheter proximally 1-2 mm, rotation of 90 degrees followed by lesion formation. As such, a longitudinal separation of lesions can occur approximately 1-2 mm apart along the longitudinal length of the distal segment of the main renal artery. For patients undergoing main artery treatment at a central segment of the main renal artery, a Symplicity Flex™ catheter can be used to form between 4 and 6 ablations in a spiral/helical pattern along the central segment of the main renal artery. For example, the first lesion can be placed approximately 5 mm proximal to the bifurcation, with each subsequent lesion placed 5 mm proximally with 90 degree rotation to form a spiral/helical pattern.

For patients undergoing renal branch treatment, modulating nerve tissue includes forming up to about four lesions (e.g., about 2 lesions to about 4 lesions) in one or more primary branch trunks (e.g., from about 1 mm to about 6 mm distal to the primary bifurcation, in regions greater than 2 mm distal to the primary bifurcation). Modulation of nerve tissue at branch trunk treatment sites and/or different combinations of treatment sites within the renal vasculature (e.g., locations along the main renal vessel, locations at or near the bifurcation, etc.) can be performed using a single-electrode Symplicity Flex™ catheter or a multi-electrode Symplicity Spyral™ catheter, both commercially available from Medtronic, Inc. Other multi-electrode, spiral/helical-shaped catheters having a tighter spiral/helix (e.g., smaller pitch) for forming multiple lesions close in proximity along the length of the vessel are contemplated for these methods. In a particular example, a method for efficaciously neuromodulating renal nerve tissue in a human patient can include advancing a single-electrode Symplicity Flex™ catheter to a first renal artery branch vessel approximately 6 mm distal to the bifurcation. A first lesion can be formed about 5-6 mm distal to the bifurcation. The catheter can then be proximally retracted 1-2 mm (e.g., maximum of 2 mm) and rotated 90 degrees followed by formation of a second lesion. Further lesions can be formed by sequential movement of the catheter proximally 1-2 mm, rotation of 90 degrees followed by lesion formation. As such, a longitudinal separation of lesions can occur approximately 1-2 mm apart along the longitudinal length of the first renal artery branch vessel (e.g., first branch trunk). In other examples, the catheter can be rotated (e.g., 90 degrees) following formation of the first lesion such that discrete lesions (e.g., non-continuous) are formed in the same longitudinal plane. Following treatment at the first renal artery branch, the catheter can be withdrawn into the main renal vessel and then advanced under fluoroscopy into a second renal artery branch and the treatment procedure can be repeated. Some methods can include treating two branch vessels at the proximal trunk segment of the branch vessel. Other methods can include treating greater than two or all of the primary branch vessels branching from the main renal vessel (e.g., distal to a primary bifurcation). As described above, these methods may also include combining neuromodulation of renal nerve tissue surrounding one or more primary branch trunks with neuromodulation of renal nerve tissue at additional treatment location (e.g., locations along the main renal vessel, locations at or near the bifurcation, etc.). Other methods can include advancing a single-electrode Symplicity Flex™ catheter to a first renal artery branch vessel approximately 10 mm distal to the bifurcation. The first lesion can be formed about 9-10 mm distal to the bifurcation, and the catheter can then be proximally retracted and rotated for forming subsequent lesions as discussed above.

Physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient having an increased risk of developing dementia (e.g., a predisposition or increased likelihood, etc.) or having one or more measurable risk factors predictive for the development of dementia, with renal neuromodulation, at one or more of the described treatment locations, will inhibit sympathetic neural activity in the renal nerve in a manner that reduces a central sympathetic drive (e.g., as correlated with whole body norepinephrine spillover and/or renal norepinephrine spillover) by greater than about 20%, about 30%, about 40%, about 50% or greater than about 60% in about 1 month, in about 3 months, in about 6 months or in about 12 months, or in another embodiment, in about 3 months to about 12 months, after renal neuromodulation treatment. Reduction in central sympathetic drive is anticipated to result in a therapeutically beneficial improvement in one or more measurable physiological risk factors corresponding to an incidence of dementia, a rate of progression of dementia, and/or a severity of dementia in the patient.

Example 7

Example 7 describes a method for determining human patients who have a risk score for developing dementia at or above a threshold dementia risk score and treating such patients with targeted sympathetic neuromodulation of renal SNS neural fibers innervating the kidney. In this example, human patients having a calculated dementia risk score meeting or exceeding a threshold dementia risk score will be treated with renal neuromodulation to improve the patient's dementia risk score and/or lower the patient's dementia risk score.

Figure 9:
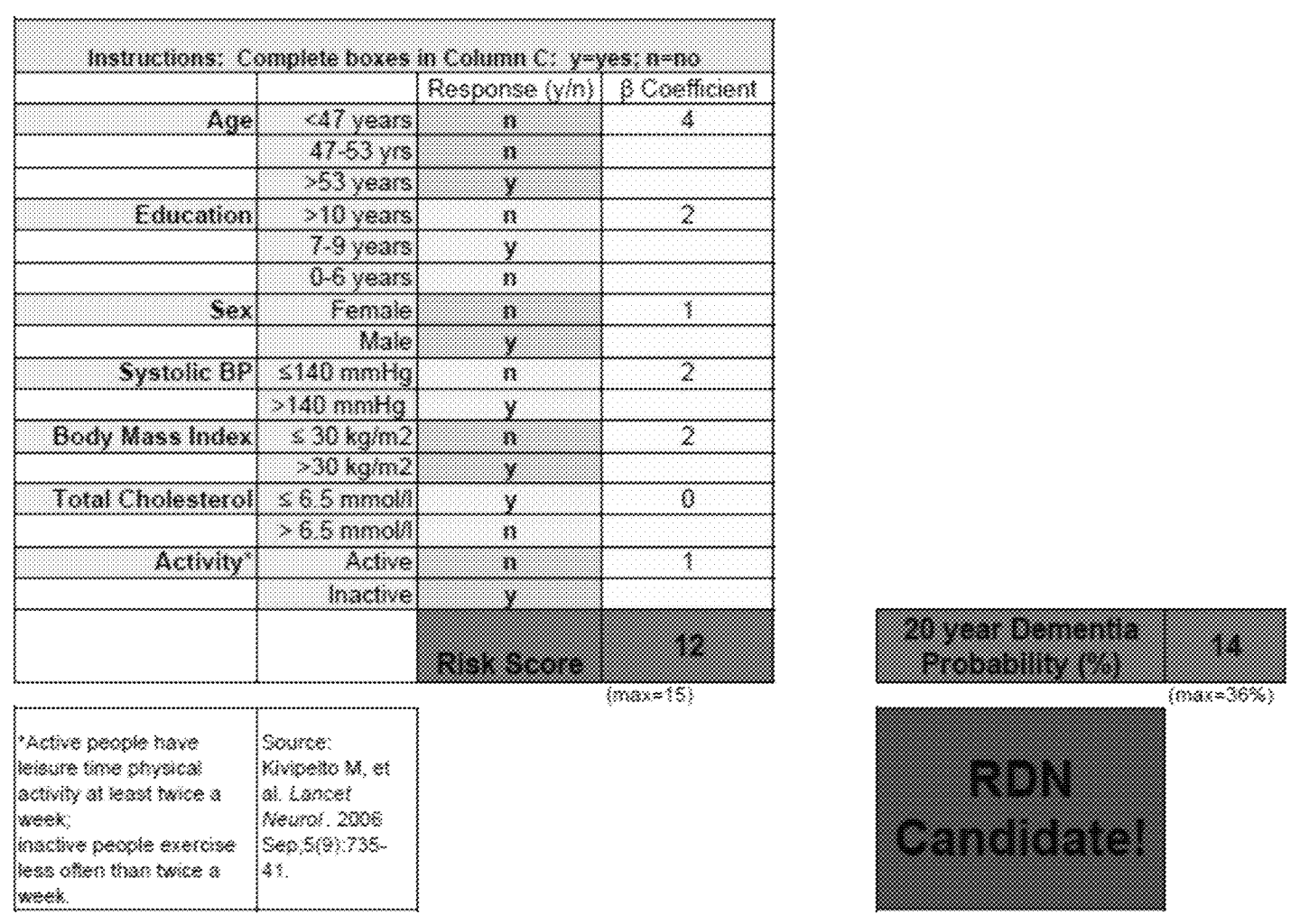

Patients presenting one or more risk factors predictive for the development of dementia will be assessed for other possible risk factors and a dementia risk score will be calculated. In this example, a patient will fill out a questionnaire or otherwise have an attending physician assess risk factors. A dementia risk score calculator based on risk factor data to determine a 20 year probability for the development of dementia in an individual is shown in FIG. 9. The dementia risk score calculator shown in FIG. 9 is derived from data provided in a study to develop a model of a technique to predict the later life risk of dementia on the basis of risk factor profiles present in middle age using data from the population-based Cardiovascular Risk Factors, Aging, and Dementia (CAIDE) study (Kivipelto, M., et al. *Lancet Neurol*, 2006, 5: 735-741).

Referring to the dementia risk score calculator shown in FIG. 9, a patient will be queried and assessed for age, education level, gender, systolic BP, body mass index, total cholesterol, and activity level. In this example, the input to the calculator will yield both a dementia risk score as well as a 20 year dementia probability (%). A threshold dementia risk score can be the dementia risk score (e.g., Risk Score of 10) as a sum of the risk factor input, or can be the calculated 20 year probability of developing dementia (e.g., 7%). As illustrated, a hypothetical 55 year old, inactive male patient with 8 years of education, having normal total cholesterol, an elevated body mass index, and having systolic BP above 140 mmHg (e.g., SBP of 150 mmHg), would exceed the threshold level determination for receiving renal neuromodulation (RDN) treatment. As illustrated, the hypothetical patient has a calculated dementia risk score of 12 and a 14% probability of developing dementia in the next 20 years. Following bilateral renal neuromodulation treatment, the hypothetical patient may have improvement in one or more measurable risk factors (e.g., systolic BP, body mass index, etc.) that improves both the dementia risk score as well as the 20 year probability of developing dementia, and in some cases, to levels below the threshold dementia risk score level(s).

VIII. FURTHER EXAMPLES

1. In a human patient under 65 years of age and diagnosed with pre-hypertension or hypertension, a method comprising:
   intravascularly positioning a neuromodulation assembly within a renal blood vessel of the patient and adjacent to a renal nerve of the patient; and
   at least partially inhibiting sympathetic neural activity in the renal nerve of the patient via the neuromodulation assembly,
   wherein at least partially inhibiting sympathetic neural activity reduces the patient's risk of developing dementia when the patient is over 65 years of age.

2. The method of example 1 wherein at least partially inhibiting sympathetic neural activity reduces a blood pressure of the patient, thereby reducing the patient's risk of developing dementia when the patient is over 65 years of age.

3. The method of example 1 or example 2 wherein reducing sympathetic neural activity in the renal nerve further reduces at least one of systolic blood pressure variability, vascular stiffness in the patient and vascular inflammation in the patient.

4. The method of any one of examples 1-3 wherein the patient has an elevated level of an inflammatory biomarker and wherein reducing sympathetic neural activity in the renal nerve further reduces the level of the inflammatory biomarker.

5. The method of example 4 wherein the inflammatory biomarker is at least one of interleukin-6 and C-reactive protein.

6. The method of any one of examples 1-5 wherein the patient has an elevated 24-hour systolic blood pressure variability, and wherein reducing sympathetic neural activity in the renal nerve further reduces the 24-hour systolic blood pressure variability in the patient.

7. The method of any one of examples 1-6 wherein the patient has had an acute ischemic stroke, and wherein reducing sympathetic neural activity in the renal nerve further reduces the patient's risk of developing dementia when the patient is over 65 years of age.

8. The method of any one of examples 1-7 wherein the patient is a carrier of at least one copy of an APOE ε4 allele, and wherein reducing sympathetic neural activity in the renal nerve further reduces the patient's risk of developing dementia when the patient is over 65 years of age.

9. The method of any one of examples 1-8 wherein reducing sympathetic neural activity in the renal nerve further reduces muscle sympathetic nerve activity (MSNA) in the patient.

10. The method of any one of examples 1-9 wherein reducing sympathetic neural activity in the renal nerve further reduces whole body norepinephrine spillover in the patient.

11. The method of example 10 wherein the whole body norepinephrine spillover is reduced by at least about 20% in about one month after reducing sympathetic neural activity in the renal nerve.

12. The method of example 10 wherein the whole body norepinephrine spillover is reduced by greater than about 40% in about three months to about 12 months after reducing sympathetic neural activity in the renal nerve.

13. In a human patient under 65 years of age, a method of reducing a risk of the patient developing dementia within 20 years, the method comprising:
   intravascularly positioning a catheter carrying a neuromodulation assembly adjacent to a renal sympathetic nerve in the patient;
   delivering energy to the renal sympathetic nerve via the neuromodulation assembly to attenuate neural traffic along the renal sympathetic nerve; and
   removing the catheter and neuromodulation assembly from the patient after treatment,
   wherein attenuating neural traffic along the renal sympathetic nerve results in one or more of—
   reducing a systolic blood pressure of the patient;
   reducing a 24-hour systolic blood pressure variability in the patient;
   reducing a level of an inflammatory biomarker in the patient;
   reducing a level of vascular stiffness in the patient; and
   increasing a level of cerebral blood flow in the patient.

14. The method of example 13 wherein the inflammatory biomarker is at least one of interleukin-6 and C-reactive protein.

15. The method of example 13 or example 14 wherein the patient has had an acute ischemic stroke, and wherein attenuating neural traffic along the renal sympathetic nerve further reduces the patient's risk of developing dementia within 20 years.

16. The method of any one of examples 1-15 wherein the patient is a carrier of at least one copy of an APOE ε4 allele, and wherein attenuating neural traffic along the renal sympathetic nerve further reduces the patient's risk of developing dementia within 20 years.

17. The method of any one of examples 1-16 wherein the patient is normotensive.

18. The method of any of examples 13-17 wherein attenuating neural traffic along the renal sympathetic nerve comprises at least partially ablating the renal sympathetic nerve.

19. The method of any one of examples 13-17 wherein attenuating neural traffic along the renal sympathetic nerve comprises at least partially disrupting communication along sympathetic neural fibers.

20. The method of any one of examples 13-17 wherein attenuating neural traffic along the renal sympathetic nerve comprises irreversibly disrupting communication along sympathetic neural fibers.

21. The method of any one of examples 13-20 wherein attenuating neural traffic along the renal sympathetic nerve comprises delivering an electrical energy field to the renal sympathetic nerve via the neuromodulation assembly.

22. The method of example 21 wherein delivering an energy field to the renal sympathetic nerve comprises delivering at least one of radio frequency energy, ultrasound energy, high intensity ultrasound energy, laser energy, and microwave energy via the neuromodulation assembly.

23. The method of any one of examples 13-22 wherein the patient is diagnosed with prehypertension or hypertension, and wherein attenuating neural traffic along the renal sympathetic nerve further reduces whole body norepinephrine spillover in the patient in a manner that reduces the risk of developing dementia within 20 years in the patient.

24. A method for improving a human patient's risk score corresponding to the development of dementia, the method comprising:
    intravascularly positioning a catheter carrying a neuromodulation assembly within a renal blood vessel and adjacent to renal nerves innervating a kidney of the patient;
    delivering energy to the renal nerves via the neuromodulation assembly to attenuate neural traffic along the renal nerves; and
    removing the catheter and neuromodulation assembly from the patient after treatment,
    wherein attenuating neural traffic along the renal nerves results in improving the patient's risk score corresponding to the development of dementia in the patient.

25. The method of example 24 wherein improving the patient's risk score corresponding to the development of dementia in the patient includes one or more of reducing the patient's blood pressure, reducing a level of systemic inflammation in the patient, and improving an atherosclerotic condition in the patient.

26. The method of example 24 or example 25 wherein improving the patient's risk score corresponding to the development of dementia in the patient includes one or more of reducing a systolic blood pressure of the patient, reducing a 24-hour systolic blood pressure variability in the patient, reducing a level of an inflammatory biomarker in the patient, reducing a level of vascular stiffness in the patient, and increasing a level of cerebral blood flow in the patient.

27. The method of example 26 wherein the inflammatory biomarker is at least one of interleukin-6 and C-reactive protein.

28. The method of any one of examples 24-27 wherein the patient is diagnosed with prehypertension or hypertension, and wherein improving the patient's risk score corresponding to the development of dementia in the patient includes reducing the patient's blood pressure.

29. The method of any one of examples 24-28 wherein a patient's risk score corresponding to the development of dementia is reduced by greater than about 10%, greater than about 15%, greater than about 20%, greater than about 30% or greater than about 40%.

30. The method of any one of examples 24-29 wherein the patient is middle-aged, and wherein attenuating neural traffic along the renal sympathetic nerve reduces a likelihood that the patient will develop dementia within 20 years.

31. The method of any one of examples 24-30 wherein the patient has had an acute ischemic stroke, and wherein attenuating neural traffic along the renal sympathetic nerve reduces a likelihood that the patient will develop dementia within 20 years.

32. The method of any one of examples 24-31 wherein the patient is a carrier of at least one copy of an APOE ε4 allele, and wherein attenuating neural traffic along the renal sympathetic nerve reduces a likelihood that the patient will develop dementia within 20 years.

33. A method for improving a dementia risk score for a human patient, the method comprising performing a renal neuromodulation procedure in the patient, wherein a determined post-neuromodulation risk score for the development of dementia within 20 years for the patient is lower than an initial risk score of the patient.

34. The method of example 33 wherein the post-neuromodulation risk score is lower than the initial risk score by about 5%, about 10%, about 20% or about 30%.

35. The method of example 33 or example 34 wherein the initial risk score indicates the patient is at risk of developing dementia within 20 years if the initial risk score is greater than a threshold risk score.

36. The method of any one of examples 33-35 wherein the initial risk score and the post-neuromodulation risk score are determined using a dementia risk score calculator tool for determining a probability of the patient developing dementia in later life.

37. The method of example 36 wherein the dementia risk score calculator tool determines a probability of the patient developing dementia within 20 years.

38. The method of any one of examples 33-37 wherein the initial risk score and the post-neuromodulation risk score are based upon one or more factors comprising age, number of years of education, gender, systolic blood pressure, body mass index, total cholesterol, activity level, systolic blood pressure variability and inflammatory biomarker level.

39. A method for preventing or slowing the progression of dementia in a patient, the method comprising:
    percutaneously introducing a neuromodulation assembly at a distal portion of a treatment device proximate to neural fibers innervating a kidney of the patient diagnosed with dementia;
    partially disrupting function of the neural fibers innervating the kidney by applying thermal energy to the neural fibers via the neuromodulation assembly; and
    removing the neuromodulation assembly from the patient after treatment,
    wherein partial disruption of the function of the neural fibers innervating the kidney therapeutically prevents or slows the progression of dementia in the patient.

40. The method of example 39 wherein the progression of dementia is assessed by one or more brain functioning tests, and wherein partial disruption of the function of the neural fibers innervating the kidney results in a decrease in a rate of decline in a test score over time.

41. The method of example 39 or example 40 wherein partial disruption of the function of the neural fibers innervating the kidney results in a therapeutically beneficial improvement in one or more measurable physiological parameters corresponding to the progression of dementia in the patient.

42. The method of example 41 wherein a measurable physiological parameter corresponding to the progression of dementia is at least one of an amount of atherosclerosis of extracranial or intracranial arteries, a measurement of large-artery stiffening, a measurement of cerebral blood flow, a measurement of blood-brain barrier disruption, a number of white mater lesions in the brain, a rate of increase in white mater lesions in the brain, a rate of increase in Lewy body formation in the brain, and a rate of cerebral atrophy in the patient.

IX. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for decreasing a human patient's risk of developing dementia, the method comprising:
   obtain, using a processor, user input that indicates one or more patient factors;
   determining, using the processor, a dementia risk score that assesses an amount of risk associated with the development of dementia in a human patient based on the user input that indicates the one or more patient factors;
   determining, using the processor, that the dementia risk score is greater than a threshold dementia risk score that represents an upper limit of an acceptable risk of dementia;
   intravascularly positioning a catheter carrying a neuromodulation assembly within a renal blood vessel and adjacent to renal nerves innervating a kidney of the human patient;
   delivering, using an energy source, energy to the renal nerves via the neuromodulation assembly to attenuate neural traffic along the renal nerves, decrease the dementia risk score and reduce a probability of dementia developing in the human patient;
   determining, using the processor, a post-neuromodulation dementia risk score that assesses the amount of risk associated with the development of dementia in the human patient after delivering the energy to the renal nerves; and
   removing the catheter and neuromodulation assembly from the human patient after treatment and when the post-neuromodulation dementia risk score is less than the dementia risk score.

2. The method of claim 1, wherein attenuating the neural traffic inhibits sympathetic neural activity in the renal nerves and causes one or more of reducing a blood pressure of the human patient, reducing a level of systemic inflammation in the human patient, and improving an atherosclerotic condition in the human patient.

3. The method of claim 1, wherein decreasing the dementia risk score includes one or more of reducing a systolic blood pressure of the human patient, reducing a 24-hour systolic blood pressure variability in the human patient, reducing a level of an inflammatory biomarker in the human patient, reducing a level of vascular stiffness in the human patient, and increasing a level of cerebral blood flow in the human patient.

4. The method of claim 3, wherein the inflammatory biomarker is at least one of interleukin-6 and C-reactive protein.

5. The method of claim 1, wherein the human patient is diagnosed with prehypertension or hypertension, and wherein decreasing the dementia risk score includes reducing a blood pressure of the human patient.

6. The method of claim 1, wherein attenuating the neural traffic along the renal nerves includes inhibiting sympathetic neural activity in the renal nerves so that the post-neuromodulation dementia risk score is at least 10% less than the dementia risk score, at least 15% less than the dementia risk score, at least 20% than the dementia risk score, at least 30% less than the dementia risk score or at least 40% less than the dementia risk score.

7. The method of claim 1, wherein the one or more patient factors include an age, a number of years of education, gender of the human patient, a cholesterol level of the human patient, smoking habits of the human patient or an activity level of the human patient.

8. The method of claim 1, further comprising:
   determining, using the processor, the probability of dementia developing in the human patient within 20 years.

9. The method of claim 1, further comprising:
comparing, using the processor, the post-neuromodulation dementia risk score to the dementia risk score.

10. The method of claim 1, further comprising:
repeatedly delivering, using the energy source, the energy to the renal nerves via the neuromodulation assembly to attenuate the neural traffic along the renal nerves until a target sympathetic nerve activity level is reached.

* * * * *